US012788934B2

(12) United States Patent
Leuthardt

(10) Patent No.: US 12,788,934 B2
(45) Date of Patent: Nov. 10, 2026

(54) RECURSIVE ARTIFICIAL INTELLIGENCE NEUROMODULATION SYSTEM

(71) Applicant: Washington University, St. Louis, MO (US)

(72) Inventor: Eric Leuthardt, St. Louis, MO (US)

(73) Assignee: Washington University, St. Louis, MO (US)

( * ) Notice: Subject to any disclaimer, the term of this patent is extended or adjusted under 35 U.S.C. 154(b) by 1139 days.

(21) Appl. No.: 17/170,553

(22) Filed: Feb. 8, 2021

(65) Prior Publication Data

US 2021/0290890 A1 Sep. 23, 2021

Related U.S. Application Data

(60) Provisional application No. 62/971,714, filed on Feb. 7, 2020.

(51) Int. Cl.
*A61M 21/00* (2006.01)

(52) U.S. Cl.
CPC ..... *A61M 21/00* (2013.01); *A61M 2021/0022* (2013.01); *A61M 2021/0027* (2013.01); *A61M 2021/0044* (2013.01); *A61M 2021/0066* (2013.01); *A61M 2021/0072* (2013.01); *A61M 2230/10* (2013.01)

(58) Field of Classification Search
CPC .............. A61M 21/00; A61M 2230/10; A61M 2205/332; A61M 2205/3553; A61M 2205/3584; A61M 2205/3592; A61M 2205/505; A61M 2209/088; A61M 2210/0693; A61B 5/165; A61B 5/4836; G16H 20/70; G16H 40/63; G16H 50/20; G16H 50/30; A61N 1/0452; A61N 1/0456; A61N 1/3603
See application file for complete search history.

(56) References Cited

U.S. PATENT DOCUMENTS

| | | | | |
|---|---|---|---|---|
| 6,416,480 B1 * | 7/2002 | Nenov | .................. | G16H 50/30 600/557 |
| 2007/0185697 A1 * | 8/2007 | Tan | ........................ | A61B 5/386 703/11 |

(Continued)

FOREIGN PATENT DOCUMENTS

| | | | | |
|---|---|---|---|---|
| WO | WO-2013069517 A1 * | 5/2013 | ........... | A61B 5/0006 |
| WO | WO-2014068537 A2 * | 5/2014 | ......... | A61B 5/02405 |

(Continued)

*Primary Examiner* — Alex M Valvis
*Assistant Examiner* — Julie Thi Tran
(74) *Attorney, Agent, or Firm* — Armstrong Teasdale LLP

(57) ABSTRACT

A brain-computer interface (BCI) system for modifying a subject's neural state are described that includes a neural activity sensor and a peripheral stimulation device operatively coupled to a computing device. A method of modifying a neural state of a subject is provided that includes receiving a target neural state from a system operator; detecting baseline neural activity signals; transforming the baseline neural activity signals into a peripheral stimulation pattern using an artificial intelligence model; administering a peripheral stimulation to the subject; detecting modified neural activity signals; and iteratively modifying the peripheral stimulation pattern to achieve a target neural state.

27 Claims, 38 Drawing Sheets
(33 of 38 Drawing Sheet(s) Filed in Color)

(56) References Cited

U.S. PATENT DOCUMENTS

| | | | | |
|---|---|---|---|---|
| 2011/0106206 | A1* | 5/2011 | Schiff | A61B 5/372 607/45 |
| 2014/0171757 | A1* | 6/2014 | Kawato | A61B 5/316 600/545 |
| 2015/0142082 | A1 | 5/2015 | Simon | |
| 2015/0199010 | A1* | 7/2015 | Coleman | H04L 67/01 345/156 |
| 2018/0285442 | A1* | 10/2018 | Coleman | G16H 10/20 |
| 2019/0212816 | A1* | 7/2019 | Myrden | A61B 5/378 |
| 2019/0247662 | A1 | 8/2019 | Alexander | |
| 2019/0387998 | A1* | 12/2019 | Garten | A61B 5/165 |

FOREIGN PATENT DOCUMENTS

| | | | | |
|---|---|---|---|---|
| WO | WO-2016112372 | A1 * | 7/2016 | A61B 5/0476 |
| WO | 2020023232 | | 1/2020 | |

* cited by examiner

RECURSIVE ARTIFICIAL INTELLIGENCE NEUROMODULATION SYSTEM

CROSS-REFERENCE TO RELATED APPLICATIONS

This application claims priority from U.S. Provisional Application Ser. 62/971,714 filed on Feb. 7, 2020, which is incorporated herein by reference in its entirety.

STATEMENT REGARDING FEDERALLY SPONSORED RESEARCH OR DEVELOPMENT

Not applicable.

FIELD OF THE DISCLOSURE

The present disclosure generally relates to devices, systems, and methods that make use of brain-computer interfaces (BCIs) to modify a neural state of a subject.

BACKGROUND OF THE DISCLOSURE

Brain computer interface (BCI) systems have emerged as a method to restore function and enhance communication in motor-impaired patients. To date, BCIs have been primarily applied to patients suffering compromised motor neuron outflow due to spinal cord dysfunction, despite an intact and functioning cerebral cortex. BCIs have also been used to treat stroke survivors with damaged hemispheres. In BCI-implemented stroke treatments, stroke survivors are trained to intentionally and effectively modulate ipsilateral motor activity from the unaffected hemisphere. This ipsilateral motor activity may be coupled with a robotic orthotic that controls hand movements of the paralyzed limbs. With ongoing use, stroke patients with chronic hand paresis were able to regain significant hand function. One prominent element of t BCI-implemented stroke treatments is the coupling of cortical activations with hand movements in real-time. When brain activations are linked with sensory feedback from the orthotic synchronously a Hebbian situation results where co-activations lead to neural remodeling and new connections (i.e. “what fires together, wires together). Without being limited to any particular theory, it is thought that this enhanced plasticity and neural remodeling translates into modulation of thalamocortical circuits.

Signals detected by electrodes on the scalp (aka EEG, electroencephalography) record lower frequency neural rhythms, including rhythms within the theta, alpha, mu, and beta bands. Without being limited to any particular theory, each of these frequency bands is thought to represent deeper structures modulating cortical excitability.

In general, BCIs are used to maximize excitability when specific stimuli are being presented. In the case of stroke, excitability is optimized when proprioceptive feedback is provided through the use of a brain-controlled orthotic controlling the paralyzed hand. A similar application of BCIs may be utilized in the context of chronic pain. Instead of altering thalamocortical rhythms for the enhancement of motor connectivity, a similar approach may be used to alter sensory circuits. Selected neural circuits can be upregulated, such that non-painful stimuli and processing are upregulated. Conversely, similar BCI feedback algorithms may be used to downregulate unwanted perceptions.

Typically, brain-computer interface approaches, including the approaches described above, involve a volitional cognitive component. Patients must use their attention to intentionally and actively control a central physiological function that then leads to a computer-driven output (mechanical movement of an orthosis or initiation of sensory stimulation). Patient perception of this computer-driven output in turn leads to a closed-loop state that can achieve an increase in desired cortical physiology and enable neural remodeling.

One challenge associated with BCI-implemented treatments as described above is that patients can become attentionally fatigued over the course of a treatment session, thus limiting the duration for how long a patient can participate in a BCI protocol. Further, patients with chronic pain are known to have reduced attention. To obviate the effects of attentional fatigue, one alternative approach is to define the desired physiology as the end goal of a brain-computer interface (BCI) system and to use an artificial intelligence model to dynamically alter a BCI-generated sensory input that is constantly updated according to a desired central response. One difference between the volitional approaches described above and the sensory input-based approaches is that the physiological changes induced by changes in the BCI-generated sensory inputs are passive in nature and controlled by an artificial intelligence algorithm. Additionally, using an AI approach will best enable the system to accommodate the non-linear relationship between sensory stimulation and the central response. Thus, a number of potential goal physiologies can be enhanced or inhibited with peripheral stimulation.

Other objects and features will be in part apparent and in part pointed out hereinafter.

SUMMARY OF THE DISCLOSURE

In one aspect, a brain-computer interface (BCI) system is disclosed that includes a neural activity sensor, a peripheral stimulation device, and a computing device operatively coupled to the neural activity sensor and the peripheral stimulation device. The neural activity sensor is configured to detect a plurality of neural activity signals indicative of a neural state of a subject. The peripheral stimulation device is configured to administer a plurality of peripheral stimulations to the subject. The computing device includes at least one processor configured to receive the plurality of neural activity signals from the neural activity sensor and to generate the plurality of peripheral stimulations based on the plurality of neural activity signals.

In another aspect, a computer-implemented method for modifying a neural state of a subject in need is disclosed. The method includes providing a brain-computer interface (BCI) system similar to the BCI system described above. The method further includes receiving, at the computing device of the BCI, a target neural state from an operator of the system; detecting, at the neural activity sensor of the BCI, a plurality of baseline neural activity signals indicative of a baseline neural state of the subject; transforming, using the computing device, the plurality of baseline neural activity signals into a peripheral stimulation pattern according to an artificial intelligence model; administering, using the peripheral stimulation device, a peripheral stimulation to the subject, the peripheral stimulation defined by the peripheral stimulation pattern; detecting, at the neural activity sensor, a plurality of modified neural activity signals indicative of a modified neural state of the subject; and iteratively modifying the peripheral stimulation pattern to match the modified neural state of the subject to the target neural state.

In an additional aspect, at least one non-transitory computer-readable storage media having computer-executable instructions embodied thereon is disclosed. When executed by at least one processor, the computer-executable instructions cause the processor to receive a target neural state from an operator of the system; receive a plurality of baseline neural activity signals indicative of a baseline neural state of the subject from a neural activity sensor; transform the plurality of baseline neural activity signals into a peripheral stimulation pattern according to an artificial intelligence model; operate a peripheral stimulation device to administer a peripheral stimulation to the subject, the peripheral stimulation defined by the peripheral stimulation pattern; receive a plurality of modified neural activity signals indicative of a modified neural state of the subject from the neural activity sensor; and iteratively modify the peripheral stimulation pattern to match the modified neural state of the subject to the target neural state.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate various aspects of the disclosure. Those of skill in the art will understand that the drawings, described below, are for illustrative purposes only. The drawings are not intended to limit the scope of the present teachings in any way.

Figure 1:
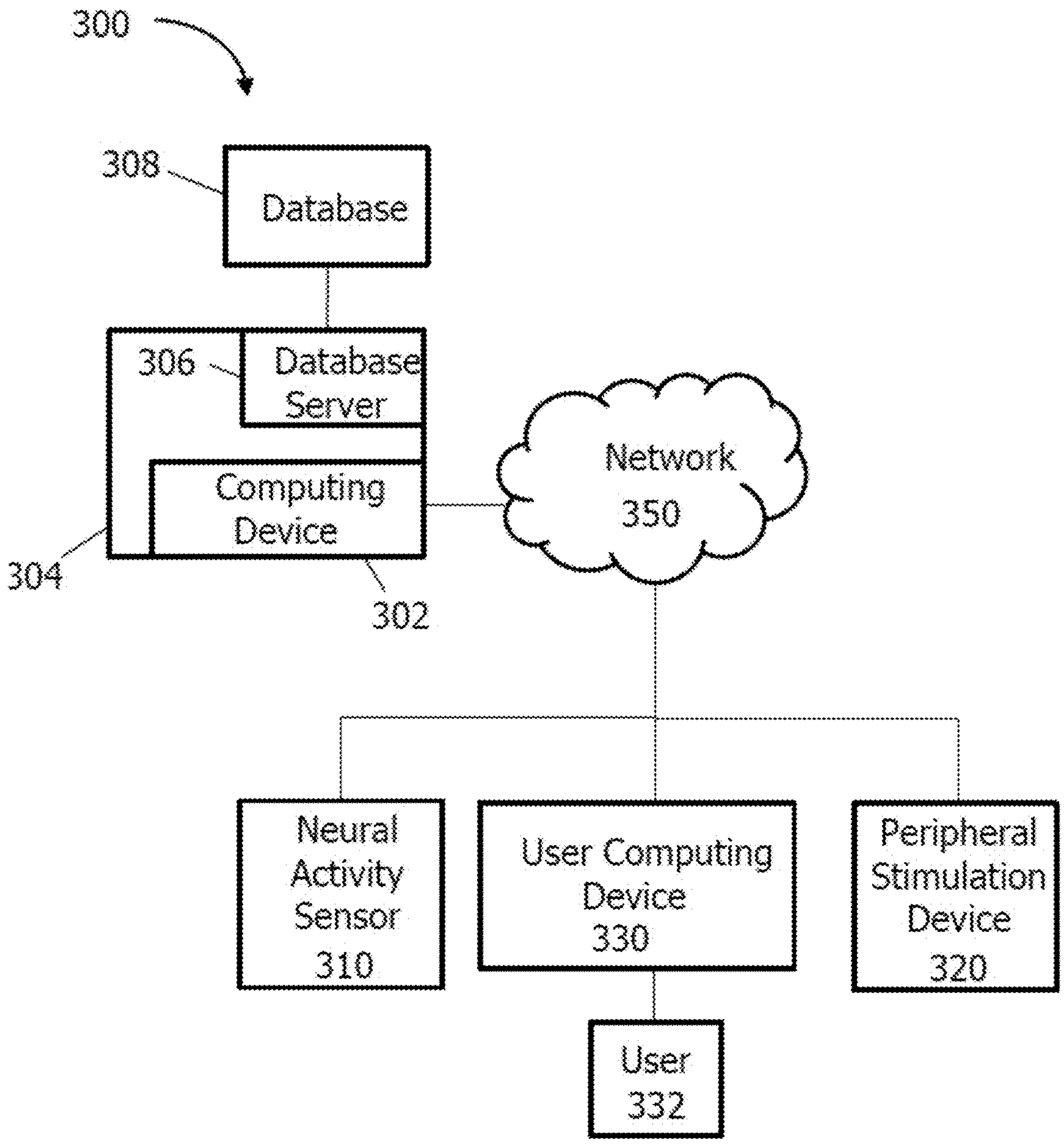
FIG. 1 is a block diagram schematically illustrating a system in accordance with one aspect of the disclosure.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION OF THE INVENTION

In various aspects, a brain-computer interface (BCI) system for modifying a neural state of a subject is disclosed. The BCI system includes a neural activity sensor for monitoring the neural state of the subject, a peripheral stimulation device configured to administer a peripheral stimulation to the subject, and a computing device operatively coupled to both the neural activity sensor and to the peripheral stimulation device. The computing device is configured to iteratively modify peripheral stimulation patterns based on changes in the neural state of the subject until the neural state of the subject is matched to a user-defined target neural state.

Unlike some existing neural modification methods, such as biofeedback, the modification of the subject's neural state occurs without a conscious or volitional effort on the part of the subject. Instead, an artificial intelligence model is used to iteratively modify the peripheral stimulation patterns administered to the subject based on the detected changes in the subject's neural state. The artificial intelligence model, including, but not limited to, a genetic model, extracts various features from the subject's neural state, develops modifications to the peripheral stimulation pattern to be administered based on changes relative to previously detected neural states of the subject, and continuously adjusts until the subject achieves the target neural state.

By way of non-limiting example, the disclosed BCI system may be used to treat a subject suffering from chronic pain. In this example, the BCI system may administer a series of peripheral stimulation patterns to the subject to achieve a neural state characterized by enhanced pre-frontal brain activity within the theta frequency range. Without being limited to any particular theory, brain activities falling within the theta frequency range are associated with relaxation, mindfulness, and meditation. Given that meditation has been previously demonstrated to improve the prognosis of chronic pain patients, it is thought that enhancing brain activity within the theta frequency range using the disclosed BCI systems and methods independently of meditation would yield similar outcomes. In one aspect, the disclosed BCI systems and methods may be used to treat chronic hand pain associated with carpal tunnel syndrome. Carpal tunnel syndrome (CTS) affects 3-6% of American adults. CTS presents with hand numbness and tingling, progressing to chronic hand pain. CTS costs the US millions each year in lost productivity and medical costs. Up to 12% of patients have symptoms that do not improve post-operatively In various aspects, the disclosed BCI system and methods implement a non-pharmacologic approach to changing brain physiology. This approach may be extremely useful for chronic pain where the brain is retrained to alter sensory perception in a part of the body that has been afflicted with chronic pain. Non-limiting examples of chronic pain disorders suitable for treatment using the disclosed BCI systems and methods include carpal tunnel syndrome, radiculopathy, painful neuropathies, complex regional pain syndrome, trigeminal neuralgia, central pain syndromes, and any other suitable chronic pain disorder.

In various other aspects, the disclosed BCI systems and methods may be used to treat a number of pathologies associated with pathologic or maladaptive physiology or network configurations. As described above, non-limiting examples of pathologies suitable for treatment using the disclosed BCI systems and methods include chronic pain, which has been associated with low frontal theta or decreased alpha in somatosensory regions. Other non-limiting examples of network pathologies that may be treated using the disclosed BCI systems and methods include depression, stroke, psychiatric diseases, ADHD, Alzheimer's, addiction, Parkinson's disease and other neurodegenerative diseases, insomnia, and sleep disorders.

Various aspects of the elements of the disclosed BCI systems and methods of treatment using the disclosed BCI systems are described in additional detail below.

I. BCI System

Figure 5:
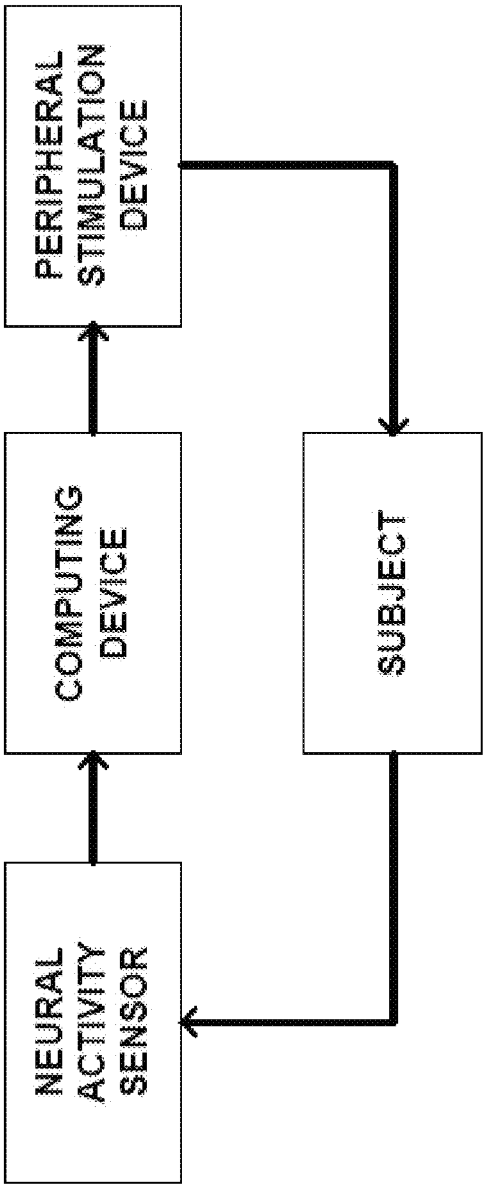
FIG. 5 is a schematic illustration of the arrangement and interface of elements of a brain-computer interface (BCI) system in accordance with one aspect of the disclosure.

A schematic diagram of the disclosed BCI system in various aspects is provided as FIG. 5. The BCI system includes a neural activity sensor, a peripheral stimulation device, and a computing device operatively coupled to the neural sensor and the peripheral stimulation device. In brief, the neural activity sensor receives a plurality of neural activity signals, such as EEG readings, from the brain of the subject that are indicative of the subject's neural state. The computing device receives the plurality of neural activity signals from the neural activity sensor, extracts one or more features from the plurality of neural activity signals, and transforms the one or more extracted features into a peripheral stimulation pattern. The computing device further operates the peripheral stimulation device, such as a vibrational stimulation device, to administer a peripheral stimulation to the subject. The peripheral stimulation is iteratively modified by the computing device using an artificial intelligence model to modify the neural state of the subject without volitional effort from the subject. The modifications could include changes in the intensity of vibration, changes in the frequency of vibration, changes in amplitude of vibration, or alternating combinations of the previously mentioned metrics.

Figure 26:
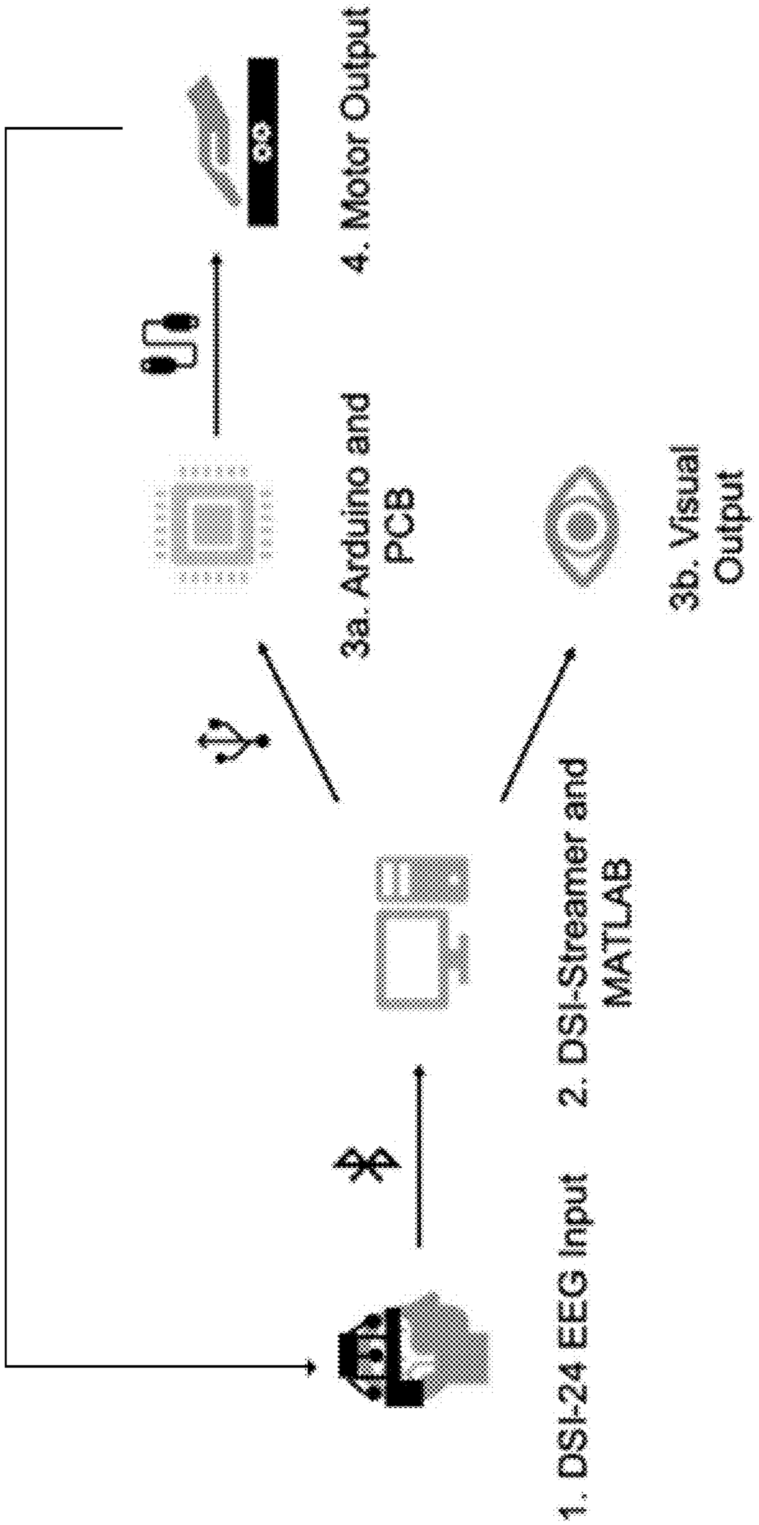
FIG. 26 is a schematic illustration of the arrangement and interface of elements of a brain-computer interface (BCI) system in accordance with one aspect of the disclosure.

FIG. 26 is a schematic diagram of an exemplary BCI system in one aspect. The neural activity sensor in this aspect is a wearable EEG array configured to detect a plurality of EEG signals that define a spatial map of neural activity within the brain of the subject. Referring again to FIG. 26. The peripheral stimulation device in this aspect is provided in the form of an array of motor discs (motor output) operated by a microcontroller board (PCB) in contact with a portion of the subject so as to deliver a spatial distribution of tactile stimuli to the subject. Also in this aspect, a computing device equipped with data acquisition software (DSI Streamer) and data processing software (MATLAB) receives EEG data from the wearable EEG array, processes the received EEG signals into a peripheral stimulation pattern, and operative the microcontroller board (PCB) to administer the peripheral stimulation via the array of motor discs.

Additional descriptions of the elements of the BCI system are provided below.

a. Neural Activity Sensor

In various aspects, the neural activity sensor may be any device capable of sensing a plurality of signals indicative of neural activity within at least a portion of a brain of a subject. In some aspects, the neural activity sensor may be a single sensing element detecting the plurality of signals at a single position relative to the subject. In other aspects, the neural activity sensor may include a plurality of sensing elements arranged in a spatial array to detect and/or map neural activity over at least one region within the brain of the subject.

In various aspects, the neural activity sensor may make use of any known invasive or non-invasive sensing modality suitable for detecting neural activity in the subject. The neural activity sensor may be selected for use in the BCI system based on any one or more criteria including, but not limited to: spatial resolution of detected neural activity, temporal resolution of detected neural activity, sensitivity of detection, ease of use, wearability or compatibility with movements of the subject, data acquisition latency, functional compatibility with other BCI system elements, relevance to a disease or diagnosis, and any other relevant criterion.

In some aspects, the neural activity sensor makes use of any suitable detection modality without limitation. Non-limiting examples of imaging modalities suitable for inclusion in a neural activity sensor of the BCI include electroencephalography (EEG), electrocorticography (ECoG), single neuron recordings, functional optical coherence tomography (fOCT), functional MRI (fMRI), magnetoencephalography (MEG), positron emission tomography (PET), functional near-infrared spectroscopy (fNIRS), single-photon emission computed tomography (SPECT) and any other functional imaging modality suitable for detecting neural activity within the brain.

In some aspects, the selected neural activity sensor may be relatively immobile and may consequently limit the locations of use of the BCI system, as is typically the case with the fMRI or MEG imaging modalities. In other aspects, the selected neural activity sensor may include portable or wearable elements, as is the case with at least some EEG and fOCT devices.

Figure 6:
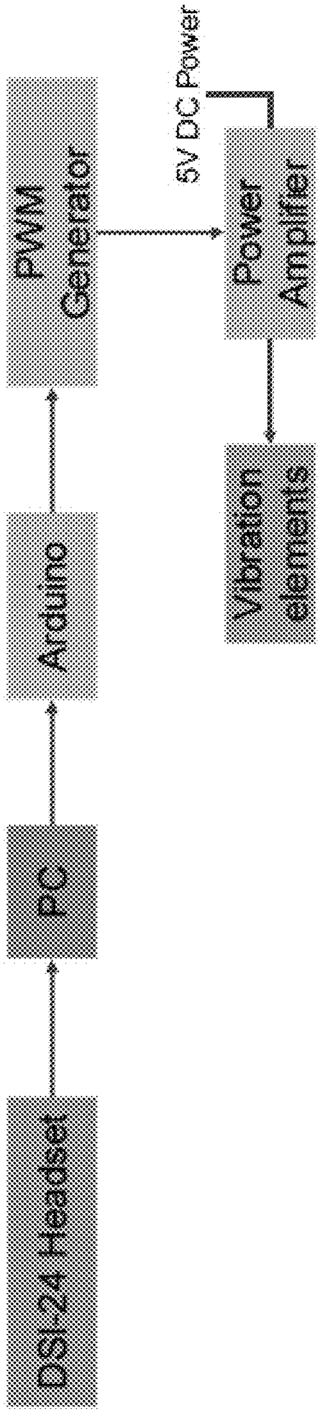
FIG. 6 is a schematic illustration of the arrangement and interface of hardware elements of the BCI system of FIG. 5 in accordance with one aspect of the disclosure.

In one exemplary aspect, the neural activity sensor is an EEG sensor, as illustrated in FIG. 6 and FIG. 26. In various aspects, the EEG sensor may include at least one EEG scalp electrode. The at least one EEG scalp electrode may be a wet electrode necessitating the application of an electrically conductive gel during use, or the at least one EEG scalp electrode may be a dry scalp electrode that may be mounted and used without the need for a gel. In one aspect, the EEG sensor may include a plurality of EEG electrodes arranged in a spatial array to facilitate the mapping of neural activity within one or more regions of the subject's brain. Non-limiting examples of brain regions of the subject that may be mapped for neural activity using the neural activity sensor include a prefrontal region, a frontal region, a central region, a parietal region, an occipital region, and a temporal region.

Figure 7:
FIG. 7 is an image of an EEG sensing device used in the BCI system of FIG. 5 in accordance with one aspect of the disclosure.

FIG. 7 shows a wearable EEG sensor array (DSI-24 Headset, Wearable Sensing, San Diego, CA, USA) in one aspect. The wearable EEG sensor array in this aspect includes 21 dry EEG electrodes positioned in an array over the scalp of the subject. The wearable EEG sensor array performs at a sampling rate of 300 Hz and may connect to a computing device via a Bluetooth connection.

b. Peripheral Stimulation Device

In various aspects, the peripheral stimulation device may be any device capable of administering a peripheral stimulation to at least one region of the subject under the control of the computing device. The peripheral stimulation is characterized as a spatial and/or temporal pattern of peripheral stimuli configured to modify the neural state of the subject as disclosed herein. The peripheral stimulation device is configured to administer peripheral stimulation using any one or more stimulation modalities including, but not limited to, tactile/mechanical stimulation such as pressure or vibration, thermal stimulation such as heating or cooling, electrical stimulation, visual stimulation such as color, shape, or motion, auditory stimulation such as pitch or loudness, and any other suitable stimulation modality. In various other aspects, the peripheral stimulation device may be capable of administering peripheral stimulations that include a combination of multiple modalities of peripheral stimulation.

In various aspects, the peripheral stimulation device may be configured to administer a peripheral stimulation to at least one region of the subject according to a peripheral stimulation pattern generated by the computing device based on the subject's currently detected neural state and the target neural state. Non-limiting examples of regions of the subject to which a peripheral stimulation may be applied include a hand region, an arm region, a leg region, a foot region, a face region, a chest region, a torso region, a pelvic region, and any other suitable region of the subject. Typically, the peripheral stimulation device is configured to administer the peripheral stimulation to the subject non-invasively to facilitate ease and comfort during use by the subject.

In various aspects, the form factor of the peripheral stimulation device may be configured to administer the peripheral stimulation to a region locally afflicted with pathologic perception. In various other aspects, the form factor of the peripheral stimulation device may be configured to administer the peripheral stimulation to one or more regions of the subject independently of whether the selected regions exhibit pathologic perception so as to modify the neural state of the subject in the form of a modified central response.

In various other aspects, the peripheral stimulation device is provided in a form factor that is best suited for delivery of the selected type of peripheral stimulus and region of the patient to which the stimulus is administered. In one non-limiting example, if the peripheral stimulation is a tactile stimulation to be administered to the hand of a subject, the form factor of the peripheral stimulation device may be sized and shaped to accommodate the hand of the subject, as described in additional detail below. In another non-limiting example, if the peripheral stimulation is visual stimulation, the form factor of the peripheral stimulation device may be a computer monitor or goggles configured to display a visual pattern as defined by the computing device.

Figure 8:
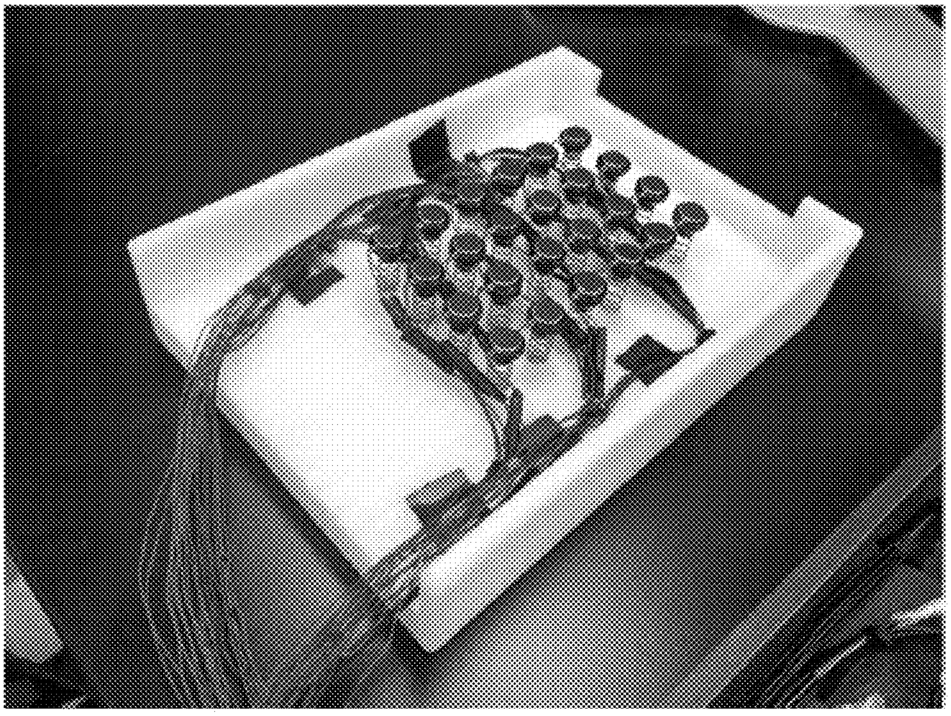
FIG. 8 is an image of a tactile feedback device used in the BCI system of FIG. 5 in accordance with one aspect of the disclosure.

In one exemplary aspect, the peripheral stimulation device is a tactile device that includes an array of motor discs, as illustrated in FIG. 8. In this aspect, the array of motor discs are arranged in a pattern in which the motor discs contact at least a portion of the region of the subject to which the peripheral stimulation is administered. Each motor disc is individually controlled to vibrate in a predetermined duration, frequency, and intensity by signals produced by a microcontroller, shown illustrated in FIG. 12 in one aspect.

Figure 9:
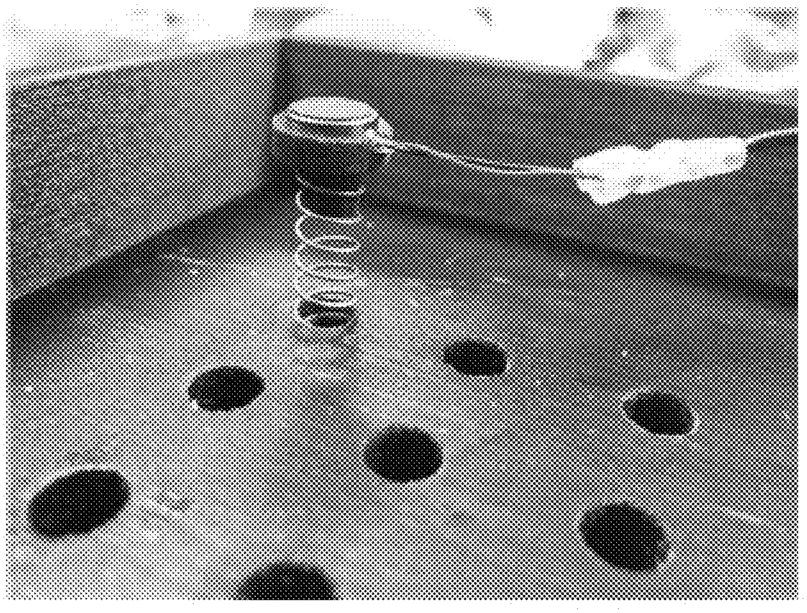
FIG. 9 is an image of an individual motor disc from the tactile feedback device of FIG. 8.

In this aspect, each motor disc may be mounted on a compressible support to provide for conformational contact of all motor units within the array with the region of the patient. Any elastic and/or compressible support may be included to support each motor disc including, but not limited to, compliant foam materials, linear actuators, elastic membranes, and individual springs, as illustrated in FIG. 9.

Figure 11:
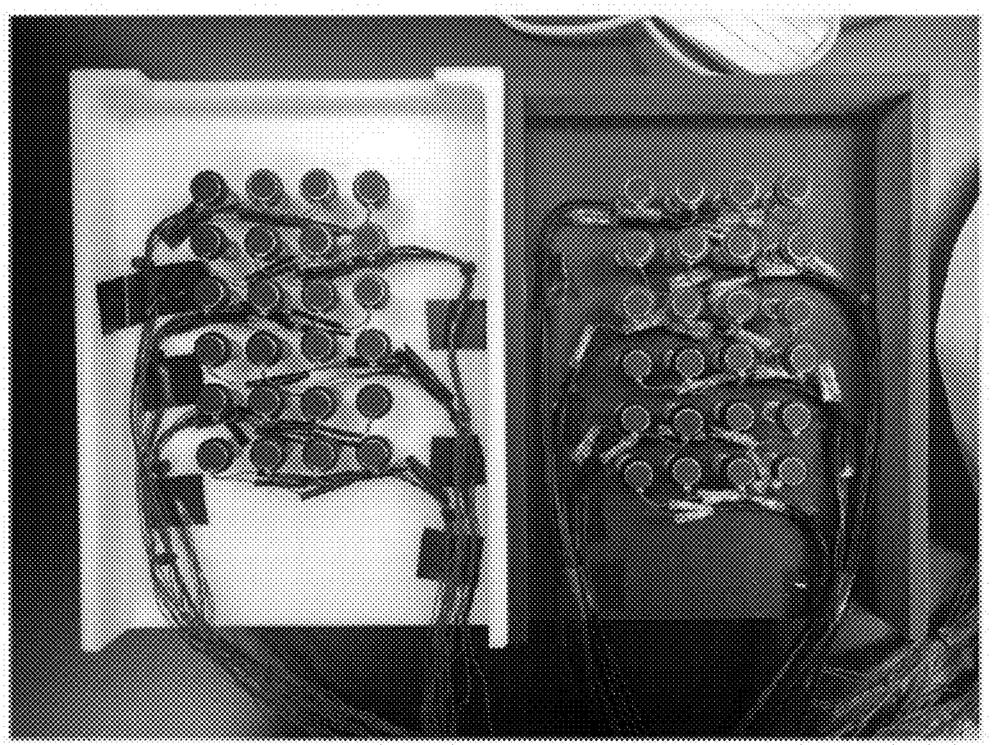
FIG. 11 is an image of an upper and lower motor disc array from the tactile feedback device of FIG. 8.

In this aspect, the array of motor discs may be arranged to deliver the tactile stimulation pattern to a single region of the subject, as illustrated in FIG. 8. In another aspect, the array of motor discs may be arranged in two or more groups, where each group is arranged to deliver a portion of the tactile stimulation pattern to a corresponding region of the subject. By way of non-limiting example, shown illustrated in FIG. 11, the array of motor discs may be arranged into a first group (left) to apply a portion of the tactile stimulation to a palm of the subject's hand and a second group (right) to apply a portion of the tactile stimulation to a back of the subject's hand. As illustrated in FIG. 11, each portion of the motor disc array includes 24 motor discs (10 mm diameter) arranged in a grid. Each half of the peripheral stimulation device illustrated in FIG. 11 occupies a volume of 8"×6"×1.5" to accommodate a hand of most subjects.

Figure 19:
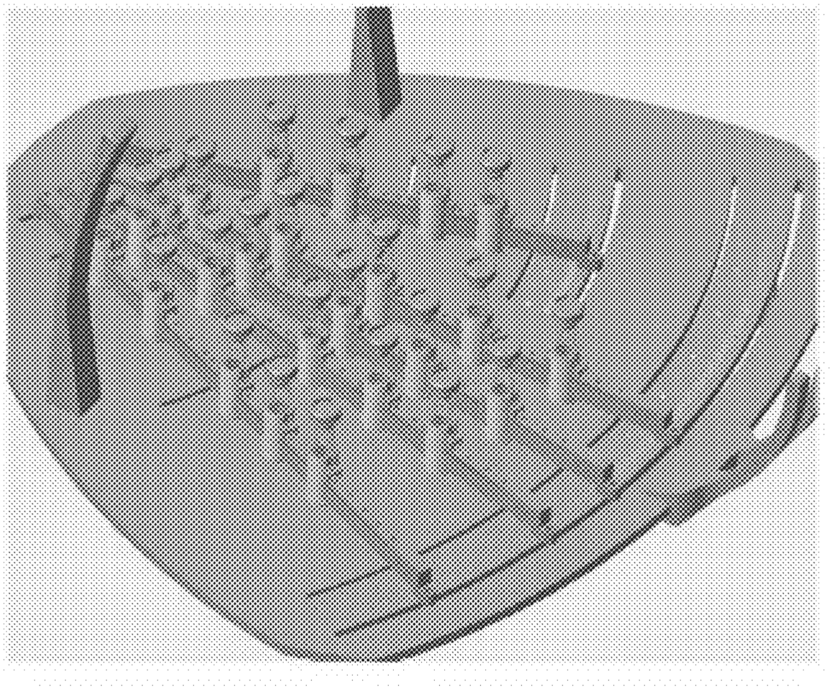
FIG. 19 is a 3D rendered drawing illustrating an inner surface of a first casing and motor disc array of a tactile feedback device in accordance with one aspect of the disclosure.
Figure 20:
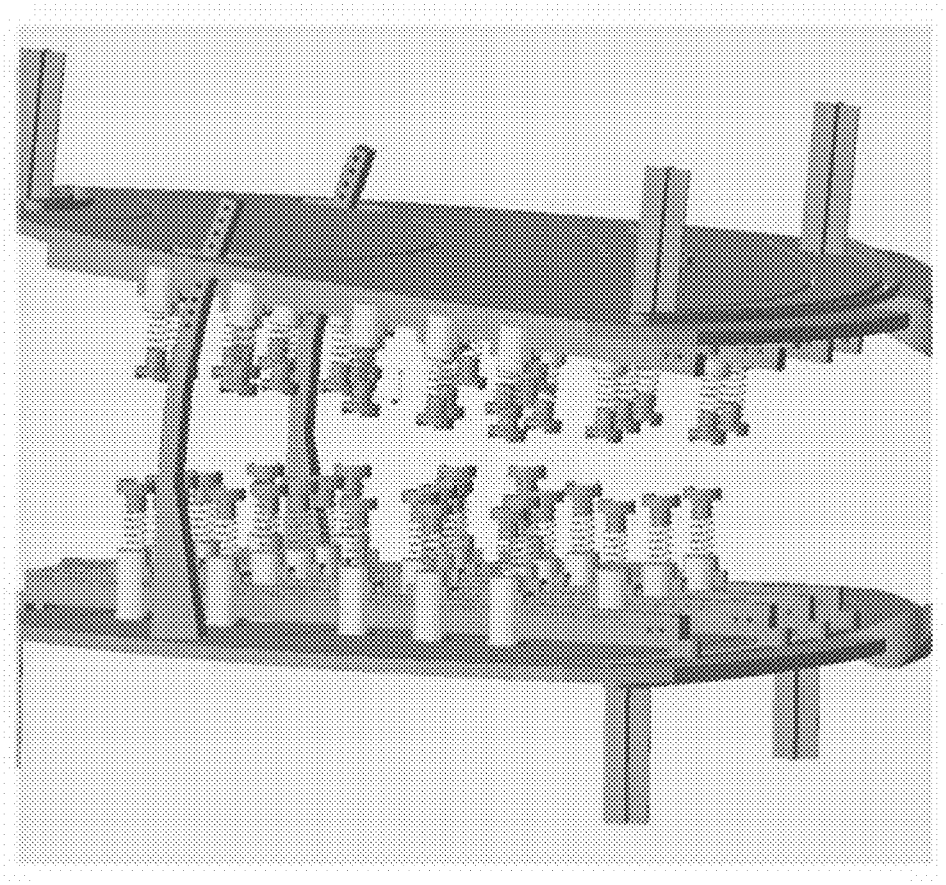
FIG. 20 is a 3D rendering illustrating the first casing and motor disc array of FIG. 19 fitted together with a second casing and motor disc array to form a tactile feedback device in accordance with one aspect of the disclosure.

In some aspects, the individual elements of the peripheral stimulation device may be positioned in a fixed position, as illustrated in FIG. 8 and FIG. 11. In other aspects, the arrangement of individual elements of the peripheral stimulation device may be adjustable to accommodate individual variations in hand size, as illustrated in FIG. 19 and FIG. 20. Referring to FIG. 19, a portion of the individual elements of the peripheral stimulation device may be mounted on repositionable supports, such as the slideable support beams shown illustrated in FIG. 19. As further illustrated in FIG. 19, in addition to sliding the support beams along corresponding slots to re-orient a linear portion of the stimulation elements (motor discs), individual elements may be repositioned along the slideable beams to adjust the spacing of the individual elements along each support beam. As illustrated in FIG. 20, the spacing of the first and second arrays of motor discs are mounted on separate plates connected by adjustable support elements to facilitate the adjustment of array separation to accommodate different hand thicknesses.

Figure 10:
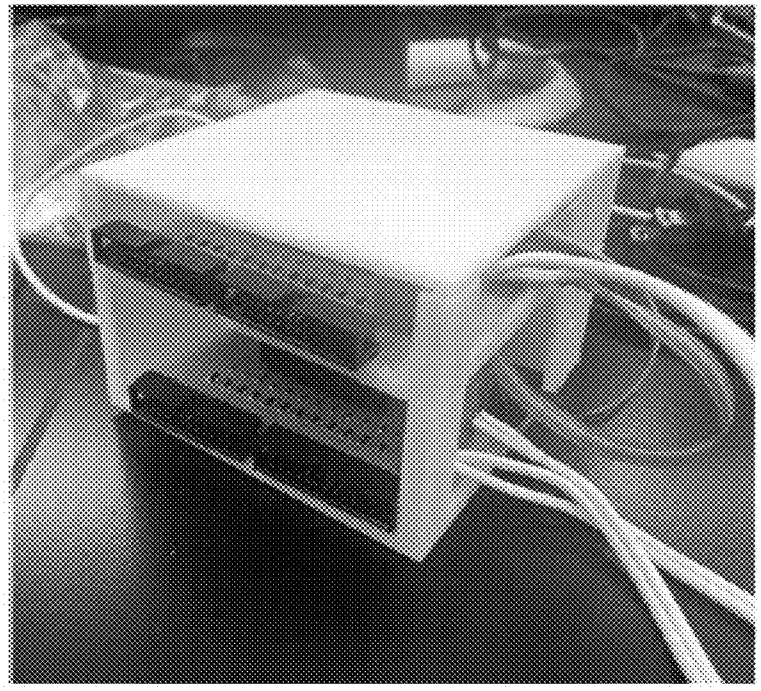
FIG. 10 is an image of a driver for the tactile feedback device of FIG. 8 in accordance with one aspect of the disclosure.
Figure 12:
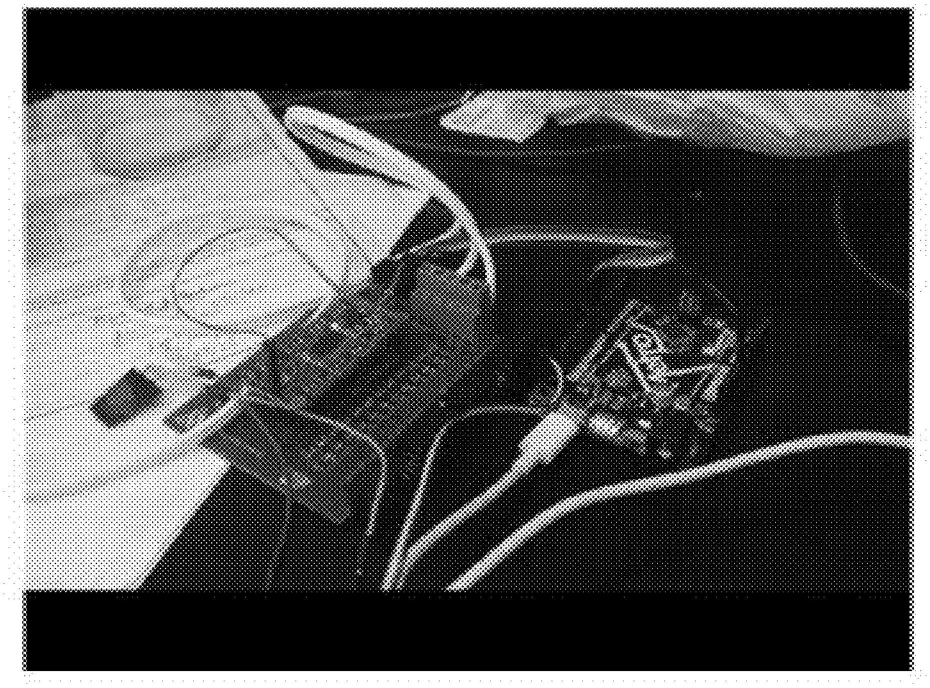
FIG. 12 is an image of a microcontroller used to operate the tactile feedback device of FIG. 8 in accordance with one aspect of the disclosure.

The control of individual elements within the peripheral stimulation device may be accomplished using any suitable control scheme and/or architecture without limitation. In one aspect, the control of all elements of the peripheral stimulation device may be accomplished using a single microcontroller, as illustrated in FIG. 12. In another aspect, separate portions of the elements of the peripheral stimulation device may be controlled with separate microcontrollers, shown illustrated in FIG. 10 and FIG. 11.

Figure 15:
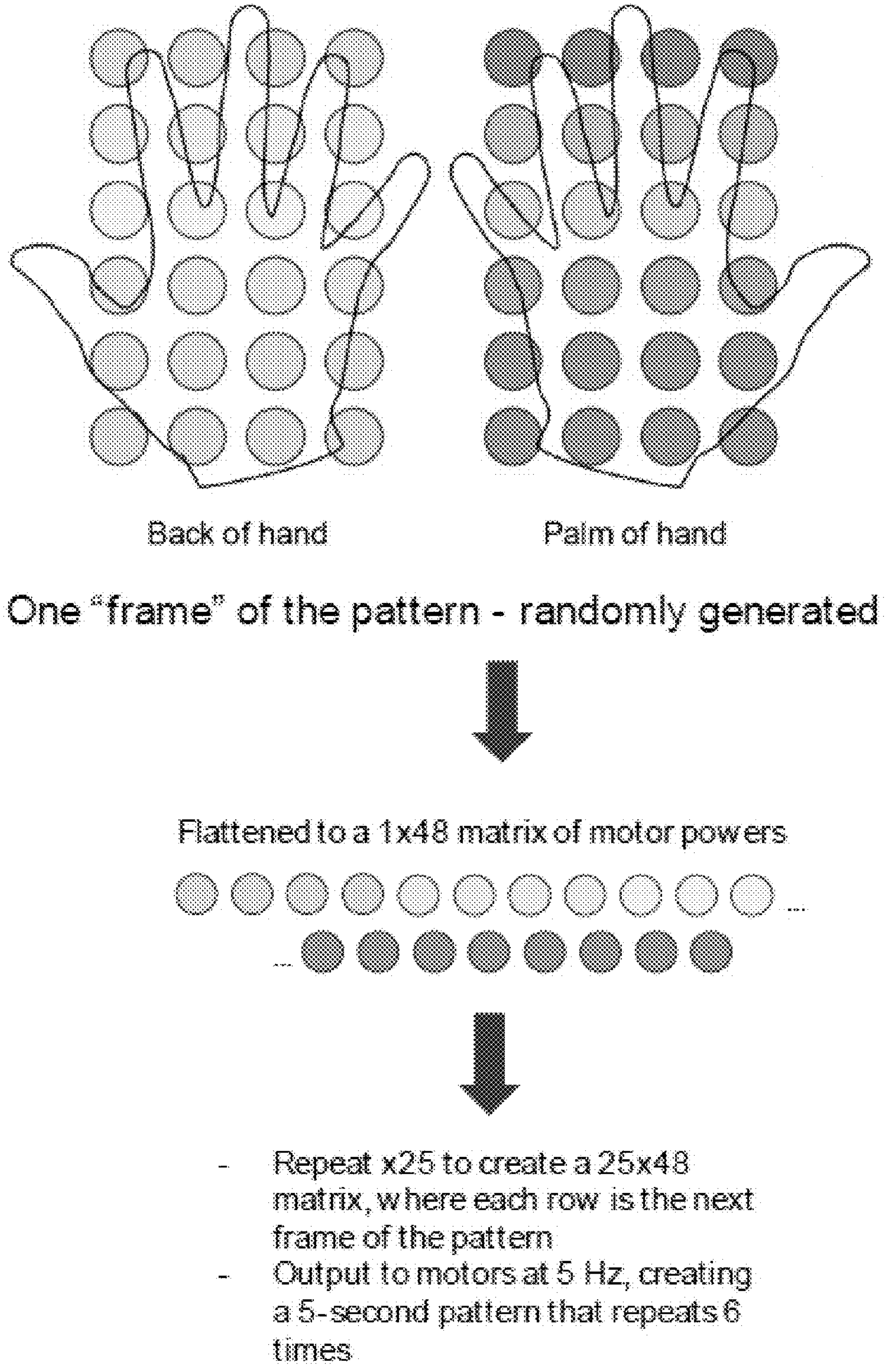
FIG. 15 is a schematic illustration of an initialization phase of the machine learning and genetic algorithm of FIG. 14 in accordance with one aspect of the disclosure.

By way of non-limiting example, one scheme for controlling the operation of the peripheral stimulation device is illustrated schematically in FIG. 15. In this example, the peripheral stimulation device includes two 4×6 arrays of motor discs, similar to the arrays illustrated in FIG. 11. Referring again to FIG. 15, each peripheral stimulus is structured as a series of frames that includes a series of motor powers corresponding to each motor disc of the two arrays. As illustrated in FIG. 15, each frame is represented as a flattened 1×48 matrix of motor powers. To assemble a peripheral stimulus, 25 frames are generated and combined to form a 25×48 matrix, in which each row of the matrix corresponds to the motor powers of one motor disc and each column corresponds to a time of one frame. The 25 frames of the matrix are played at a rate of 5 Hz to administer a 5-second pattern of activation of the motor disc arrays.

In various aspects, a peripheral stimulus may be characterized in the form of a matrix that includes a series of frames, each frame corresponding to a column of the matrix. In one aspect, the overall duration of a peripheral stimulus may be defined by at least one or more parameters including, but not limited to, the number of frames defining the stimulus, the playback rate of the peripheral stimulus, and any other suitable parameter. Within each frame, at least one or more frame parameters define the operation of each element of the peripheral stimulation device at each time point within the peripheral stimulus. Non-limiting examples of suitable frame parameters include element activation timing, intensity of activation, waveform, spatial positioning, duration, and any other relevant aspect of the operation of individual elements of the peripheral stimulus device.

In various aspects, the peripheral stimulus matrix is generated by the computing device as described in additional detail below. In some aspects, a peripheral stimulus matrix may be generated by the computing device using a random algorithm. In other aspects, the peripheral stimulus device may generate a series of peripheral stimulus matrices according to an artificial intelligence algorithm that modifies each successive stimulus matrix based on changes in the neural state of the subject detected by the neural activity sensor.

In various aspects, the individual elements of the peripheral stimulus device are operated by transmitting a plurality of electrical signals to control the time course of operation of each element including, but not limited to, a waveform of the element output intensity. Any known method of operating individual stimulation elements may be incorporated into the peripheral stimulus device without limitation. By way of non-limiting example, FIG. 6 provides a schematic illustration of control elements that may be used to operate the peripheral stimulus device in one aspect. As illustrated in FIG. 6, a microcontroller (Arduino) may be used to control the operation of a pulse-width modulated (PWM) waveform generator used to generate PWM signals that are amplified by a power amplifier and to drive individual motor discs (vibration elements). Referring again to FIG. 6, the computing device (PC) may produce and transmit a series of peripheral stimulus matrices to the microcontroller based on EEG signals received from the neural state sensor (DSI-24 Headset) and processed using an artificial intelligence model.

c. Computing Device

In various aspects, the BCI system further includes a computing device operatively coupled to the neural activity sensor and peripheral stimulation device, as illustrated in FIGS. 5, 6, and 26. The computing device receives and records brain signals detected by the neural activity sensor, computationally processes the brain signals in real-time to extract features of brain signals, and dynamically controlling the operation of the peripheral stimulation device based on the extracted features using an artificial intelligence algorithm.

FIG. 1 depicts a simplified block diagram of a computing device 300 for implementing the methods described herein. As illustrated in FIG. 1, the computing device 300 may be configured to implement at least a portion of the tasks associated with the method of modifying a neural state of a subject by administering a peripheral stimulation using the peripheral stimulation device 320 based on analysis of a plurality of signals indicative of a neural state of the subject obtained using the neural activity sensor 310. The computer system 300 may include a computing device 302. In one aspect, the computing device 302 is part of a server system 304, which also includes a database server 306. The computing device 302 is in communication with a database 308 through the database server 306. The computing device 302 is communicably coupled to a neural activity sensor 310, a peripheral stimulation device 320, and a user computing device 330 through a network 350. The network 350 may be any network that allows local area or wide area communication between the devices. For example, the network 350 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user computing device 330 may be any device capable of accessing the Internet including, but not limited to, a desktop computer, a laptop computer, a personal digital assistant (PDA), a cellular phone, a smartphone, a tablet, a phablet, wearable electronics, smartwatch, or other web-based connectable equipment or mobile devices.

Figure 2:
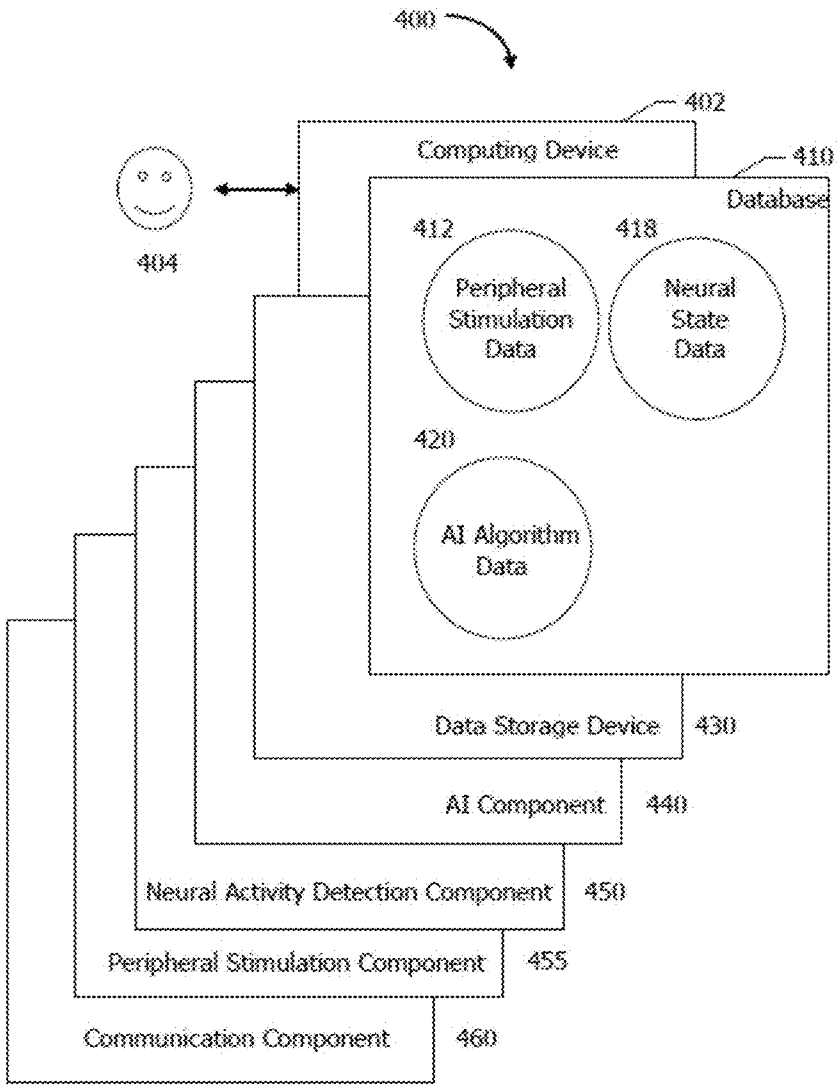
FIG. 2 is a block diagram schematically illustrating a computing device in accordance with one aspect of the disclosure.

In other aspects, the computing device 302 is configured to perform a plurality of tasks associated with the disclosed method of modifying the neural state of a subject using an artificial intelligence model. FIG. 2 depicts a component configuration 400 of computing device 402, which includes database 410 along with other related computing components. In some aspects, computing device 402 is similar to computing device 302 (shown in FIG. 1). A user 404 may access components of computing device 402. In some aspects, database 410 is similar to database 308 (shown in FIG. 1).

In one aspect, database 410 includes neural state data 418, artificial intelligence (AI) algorithm data 420, and peripheral stimulation data 412. Non-limiting examples of suitable AI algorithm data 420 includes any values of parameters defining the AI model used to extract features from the plurality of brain signals indicative of a neural state of the subject and to administer a series of peripheral stimulations to the subject based on the extracted brain signal features. In one aspect, the peripheral stimulation data 412 includes any values defining the operation of the peripheral stimulation device to administer peripheral stimulations to the subject to modify the neural state of the subject as described herein. In one aspect, the neural state data 418 includes any values defining the previous, current, and target neural states of the subject, including, but not limited to, brain signals received from the neural activity sensor and extracted features of the brain signals.

Computing device 402 also includes a number of components that perform specific tasks. In the exemplary aspect, the computing device 402 includes a data storage device 430, AI component 440, neural activity detection component 450, peripheral stimulation component 455, and communication component 460. The data storage device 430 is configured to store data received or generated by computing device 402, such as any of the data stored in database 410 or any outputs of processes implemented by any component of computing device 402. The neural activity detection component 450 is configured to operate or produce signals configured to operate the peripheral stimulation device 320 (FIG. 1) to administer one or more peripheral stimulations to the subject to modify the subject's neural state.

AI component 440 is configured to extract features of the brain signals obtained using the neural activity detection component 450, and administer one or more peripheral stimulations based on the extracted features using the peripheral stimulation component 455. In various aspects, the AI component 440 may implement any suitable AI model or algorithm without limitation including, but not limited to, genetic algorithms, linear or logistic regression algorithms, instance-based algorithms, regularization algorithms, decision tree algorithms, Bayesian network algorithms, cluster analysis algorithms, association rule learning, supervised learning, unsupervised learning, reinforcement learning, artificial neural networks, deep learning, dimensionality reduction algorithms, and support vector machines.

The communication component 460 is configured to enable communications between computing device 402 and other devices (e.g. user computing device 330, neural activity sensor 310, and peripheral stimulation device 320, shown in FIG. 1) over a network, such as a network 350 (shown in FIG. 1), or a plurality of network connections using predefined network protocols such as TCP/IP (Transmission Control Protocol/Internet Protocol).

Figure 3:
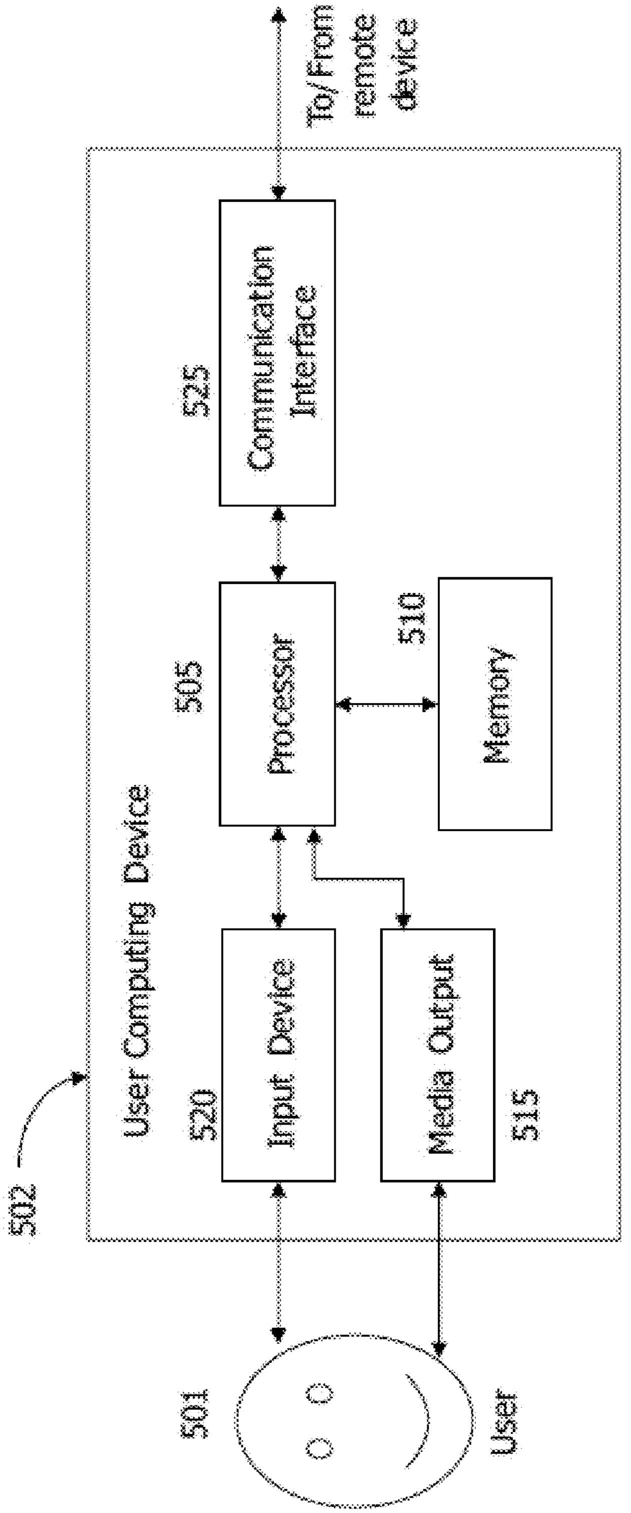
FIG. 3 is a block diagram schematically illustrating a remote or user computing device in accordance with one aspect of the disclosure.

FIG. 3 depicts a configuration of a remote or user computing device 502, such as user computing device 330 (shown in FIG. 1). Computing device 502 may include a processor 505 for executing instructions. In some aspects, executable instructions may be stored in a memory area 510. Processor 505 may include one or more processing units (e.g., in a multi-core configuration). The memory area 510 may be any device allowing information such as executable instructions and/or other data to be stored and retrieved. Memory area 510 may include one or more computer-readable media.

Computing device 502 may also include at least one media output component 515 for presenting information to a user 501. Media output component 515 may be any component capable of conveying information to user 501. In some aspects, media output component 515 may include an output adapter, such as a video adapter and/or an audio adapter. An output adapter may be operatively coupled to processor 505 and operatively couplable to an output device such as a display device (e.g., a liquid crystal display (LCD), an organic light-emitting diode (OLED) display, cathode ray tube (CRT), or "electronic ink" display) or an audio output device (e.g., a speaker or headphones). In some aspects, media output component 515 may be configured to present an interactive user interface (e.g., a web browser or client application) to user 501.

In some aspects, computing device 502 may include an input device 520 for receiving input from user 501. Input device 520 may include, for example, a keyboard, a pointing device, a mouse, a stylus, a touch-sensitive panel (e.g., a touchpad or a touch screen), a camera, a gyroscope, an accelerometer, a position detector, and/or an audio input device. A single component such as a touch screen may function as both an output device of media output component 515 and input device 520.

Computing device 502 may also include a communication interface 525, which may be communicatively couplable to a remote device. Communication interface 525 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 510 are, for example, computer-readable instructions for providing a user interface to user 501 via media output component 515 and, optionally, receiving and processing input from input device 520. A user interface may include, among other possibilities, a web browser and client application. Web browsers enable users 501 to display and interact with media and other information typically embedded on a web page or a website from a web server. A client application allows users 501 to interact with a server application associated with, for example, a vendor or business.

Figure 4:
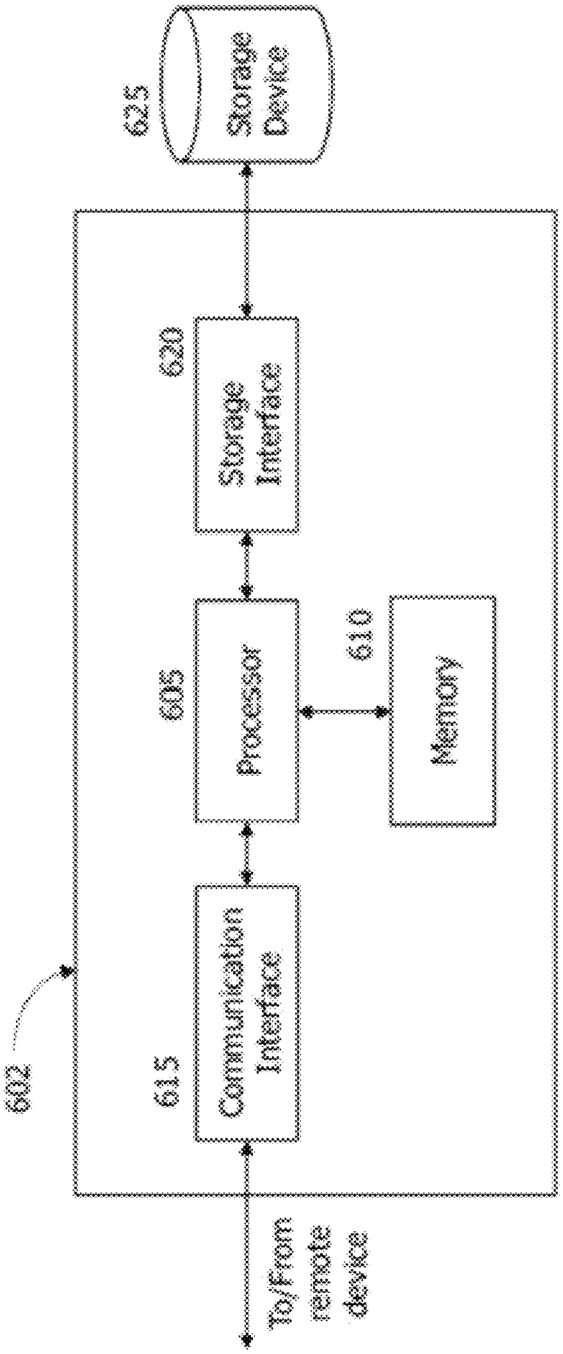
FIG. 4 is a block diagram schematically illustrating a server system in accordance with one aspect of the disclosure.

FIG. 4 illustrates an example configuration of a server system 602. Server system 602 may include, but is not limited to, database server 306 and computing device 302 (both shown in FIG. 1). In some aspects, server system 602 is similar to server system 304 (shown in FIG. 1). Server system 602 may include a processor 605 for executing instructions. Instructions may be stored in a memory area 625, for example. Processor 605 may include one or more processing units (e.g., in a multi-core configuration).

Processor 605 may be operatively coupled to a communication interface 615 such that server system 602 may be capable of communicating with a remote device such as user computing device 330 (shown in FIG. 1) or another server system 602. For example, communication interface 615 may receive requests from the user computing device 330 via a network 350 (shown in FIG. 1).

Processor 605 may also be operatively coupled to a storage device 625. Storage device 625 may be any computer-operated hardware suitable for storing and/or retrieving data. In some aspects, storage device 625 may be integrated into server system 602. For example, server system 602 may include one or more hard disk drives as storage device 625. In other aspects, storage device 625 may be external to server system 602 and may be accessed by a plurality of server systems 602. For example, storage device 625 may include multiple storage units such as hard disks or solid-state disks in a redundant array of inexpensive disks (RAID) configuration. Storage device 625 may include a storage area network (SAN) and/or a network-attached storage (NAS) system.

In some aspects, processor 605 may be operatively coupled to storage device 625 via a storage interface 620. Storage interface 620 may be any component capable of providing processor 605 with access to storage device 625. Storage interface 620 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 605 with access to storage device 625.

Memory areas 510 (shown in FIG. 3) and 610 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are examples only and are thus not limiting as to the types of memory usable for the storage of a computer program.

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on a vehicle or mobile devices, or associated with smart infrastructure or remote servers), and/or via computer-executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on the motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: genetic algorithms, linear or logistic regressions, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

Referring to FIG. 2, the AI component 440 (FIG. 2) of the computing device 402 applies a genetic algorithm to extract features of brain waves obtained using the neural activity detection component 450 and to produce at least one peripheral stimulus based on the extracted features to be administered using the peripheral stimulation component 455 in one aspect.

In various aspects, the genetic algorithm represents peripheral stimulation patterns as described above (see FIG. 15) as "genes". According to the genetic algorithm, the plurality of parameters characterizing the peripheral stimulation pattern is represented as "base pairs". By way of non-limiting example, each peripheral stimulation pattern as illustrated in FIG. 15 and described above includes a peripheral stimulation matrix that includes 1200 base pairs that include 25 frames in which each frame includes 48 parameters defining the operation of the individual elements from the two motor disc arrays of the peripheral stimulation device.

Figure 17:
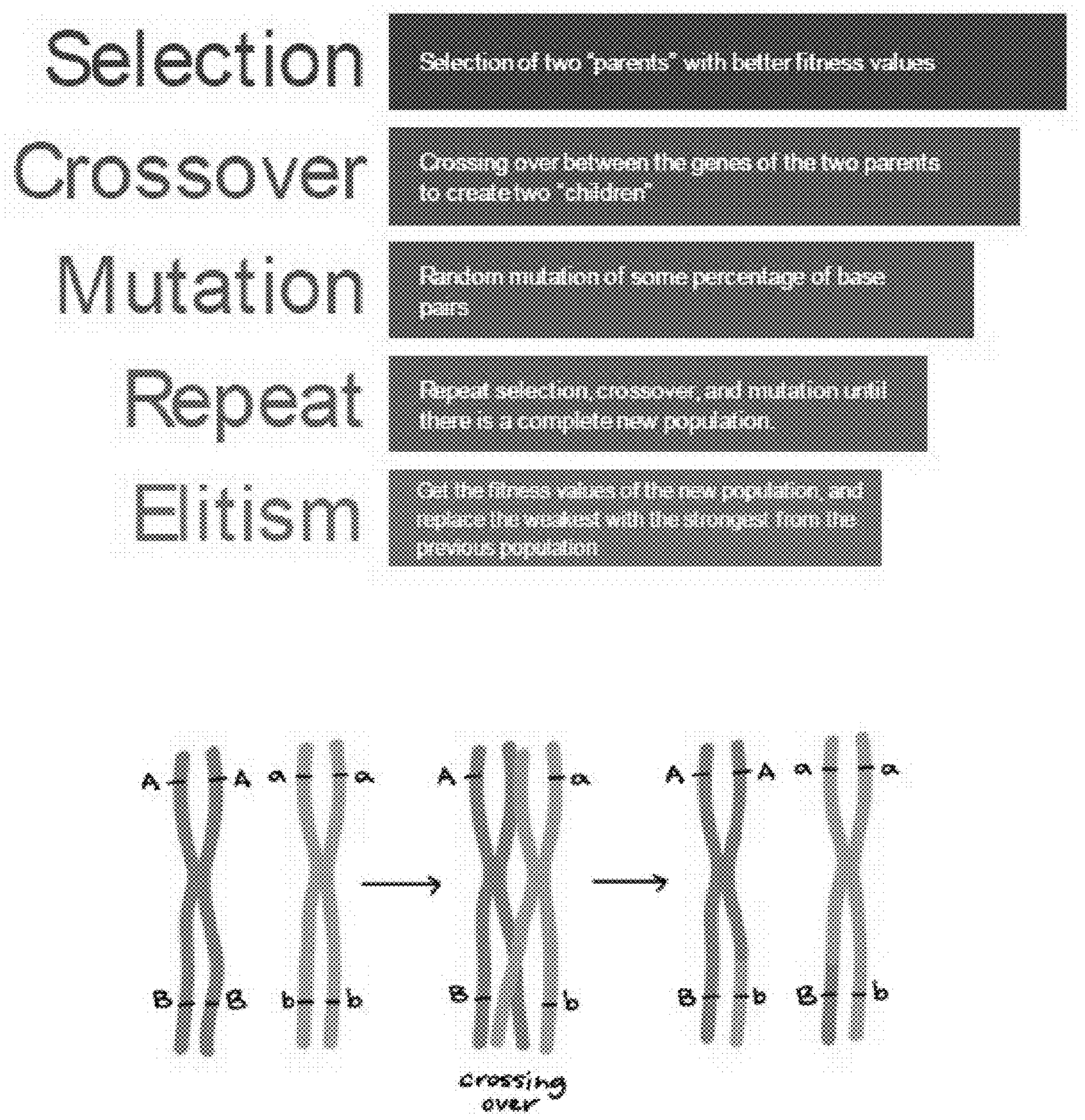
FIG. 17 is a schematic illustration of various processes of the machine learning and genetic algorithm of FIG. 14.

According to the genetic algorithm, the "gene" representing the peripheral stimulation pattern is modified using principles analogous to genetic modification. Non-limiting examples of analogous methods of genetic modification suitable for implementation using the genetic algorithm include selection, crossover, mutation, base-pair repeats, and elitism, all of which are shown illustrated in FIG. 17.

Figure 16:
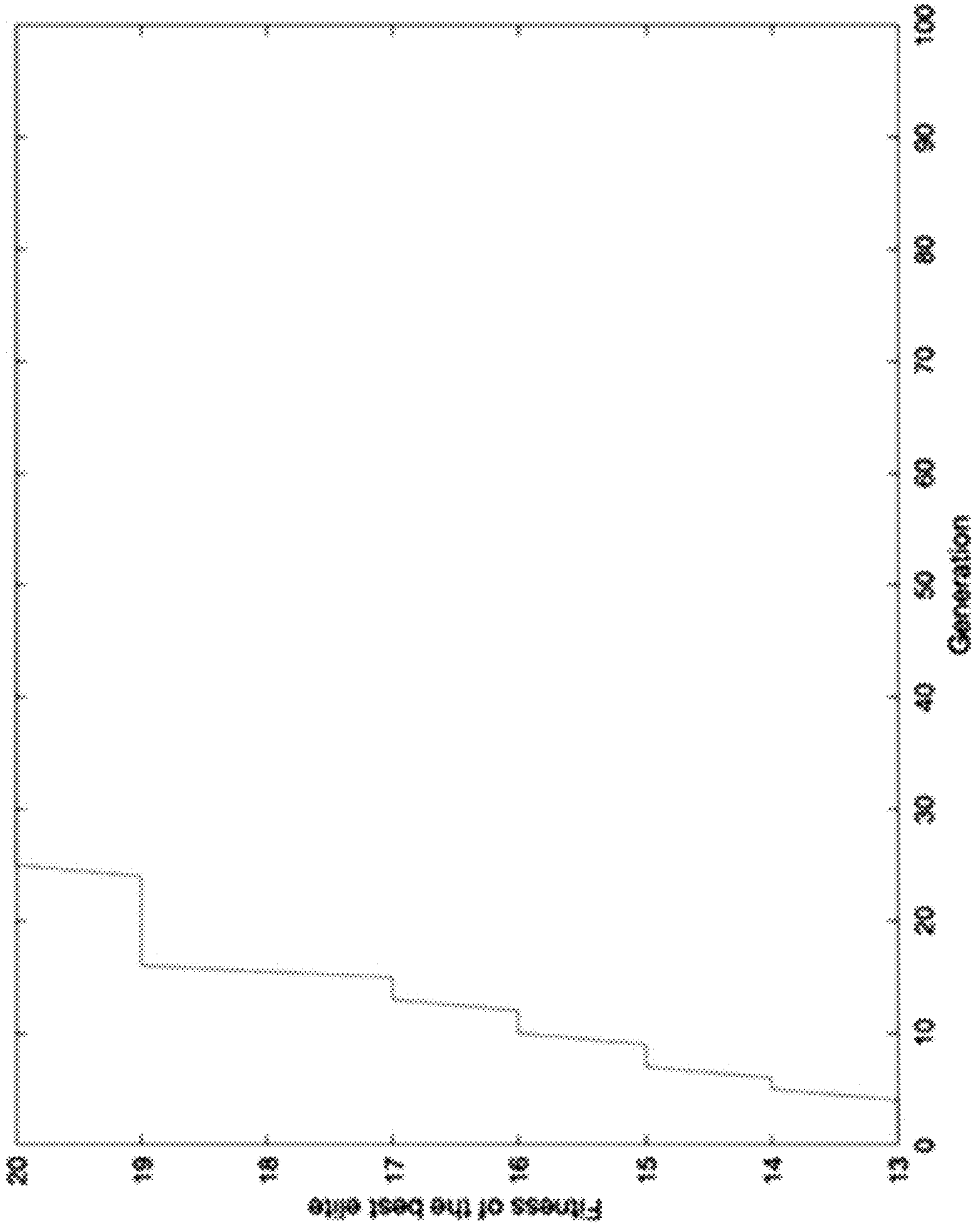
FIG. 16 is a graph representing a fitness parameter used to select successive iterations of tactile stimulation patterns according to the machine learning and genetic algorithm of FIG. 14.

In addition, the administration of the peripheral stimulation pattern to the subject is analogous to "expression" of the "gene", in which the product of gene expression is a modification of the neural state of the subject. Each peripheral stimulation pattern generated using the peripheral stimulation device is associated with a modification of the subject's neural state, as detected using the neural activity sensor. Modifications of the subject's neural state are used to assess the "fitness" of the gene, as illustrated in FIG. 16. In various aspects, this "fitness" corresponds to a target neural state of the subject.

In various aspects, the genetic algorithm may be used to iteratively modify a peripheral stimulation pattern to transition a subject's neural state from a baseline neural state to a target neural state. Typically, the target neural state includes any neural state associated with the alleviation of a symptom to be treated. By way of non-limiting example, the target neural state may be enhanced neural activity within the theta and/or alpha frequency range, which have been associated with the reduction of chronic pain symptoms.

Figure 14:
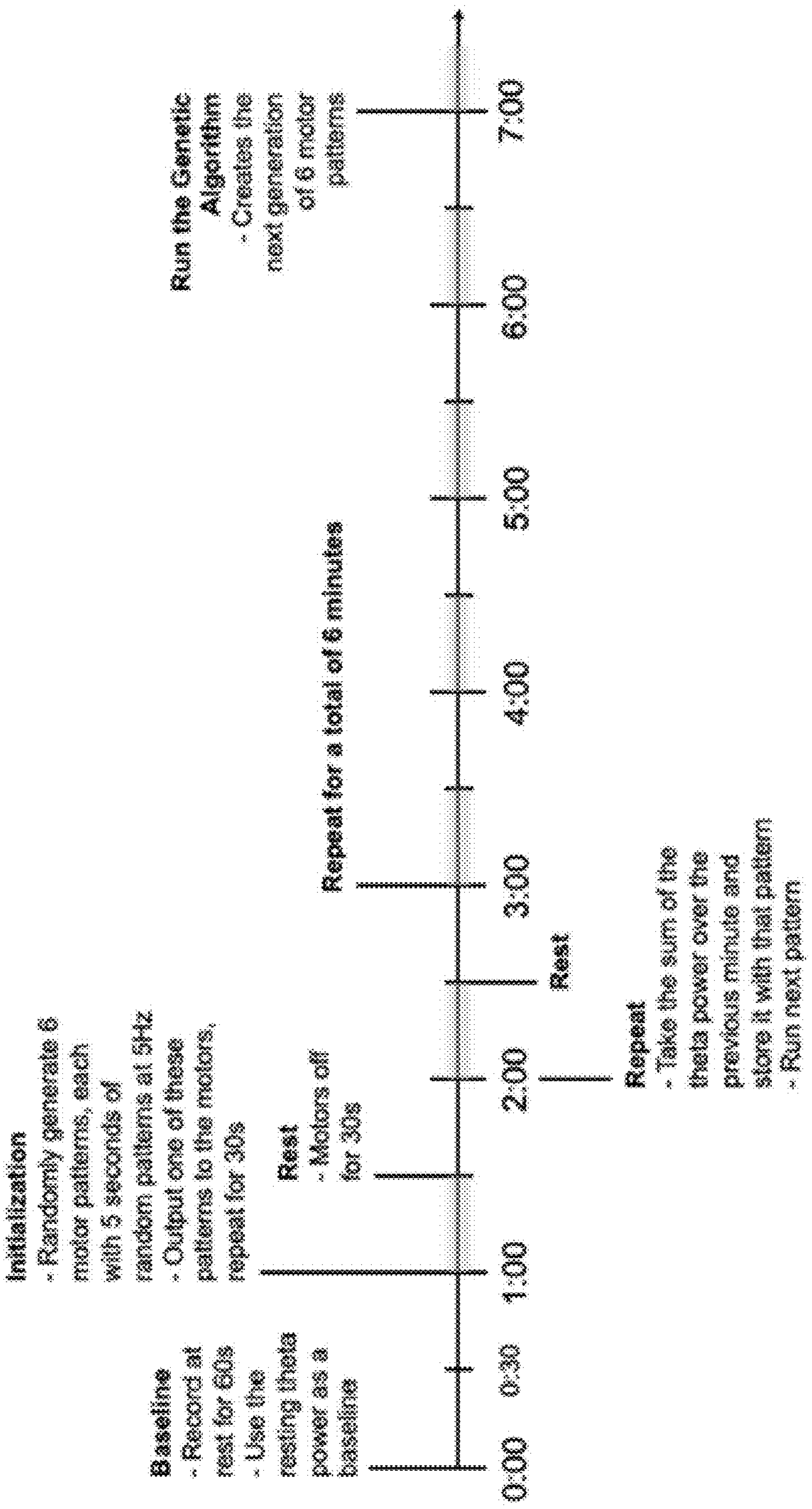
FIG. 14 is a timeline representation of a machine learning and genetic algorithm in accordance with one aspect of the disclosure.
Figure 18:
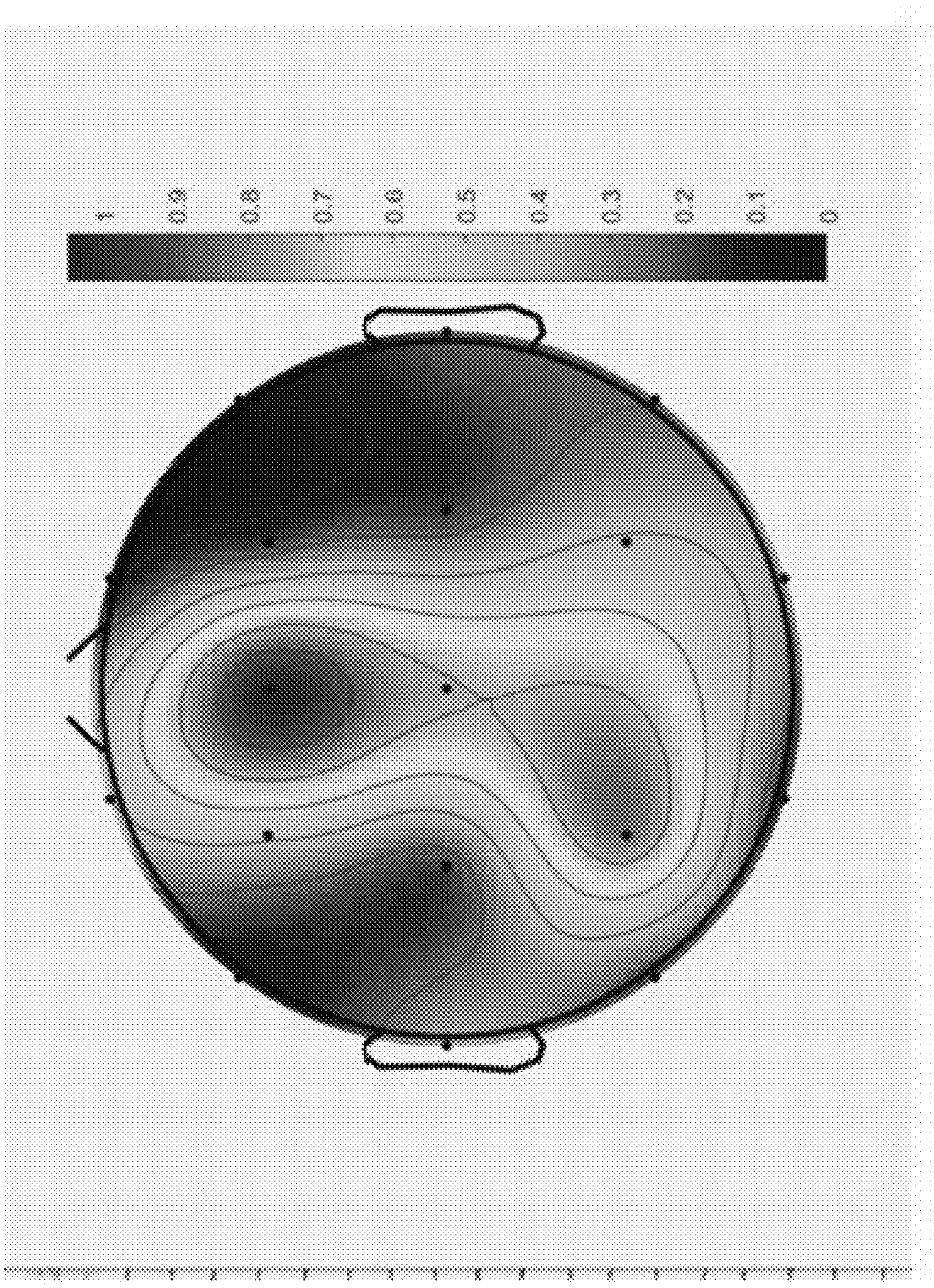
FIG. 18 is a screenshot of a map of theta power obtained from a subject using the BCI system of FIG. 5.

By way of non-limiting example, the genetic algorithm may be used to modify a peripheral stimulation pattern administered to a subject in order to achieve a target neural state characterized by enhanced neural activity within the theta frequency range, as illustrated in FIG. 14. In this non-limiting example, the target neural state is characterized by increased frontal theta frequency amplitude (3-5 Hz). These rhythms are associated with meditative states and pain relief. The subject would wear an EEG headset (FIG. 7) which is connected to the computing device, which is also connected to a wearable system that has multiple vibration elements on the palmar and dorsal aspects of the hand (FIG. 11). Referring again to FIG. 14, the BCI system monitors neural activity for 60 seconds using the neural activity sensor to establish a baseline neural state. Subsequently, the BCI system administers a random regime of peripheral stimulation patterns characterized by vibrations at different frequencies and different locations of the hand. The BCI system would then use the AI algorithm (e.g. genetic algorithm) to iteratively reconfigure the stimulation pattern based on the ongoing increases in the theta frequency power (see FIG. 18) as detected using the neural activity sensor. Over time, as successive peripheral stimulation patterns are administered, the frontal theta power will consistently increase, as reflected by the step-wise fitness increases illustrated in FIG. 16. Significantly, the AI algorithm (e.g. genetic algorithm) detects non-linear relationships between the peripheral stimulation patterns and the response in the brain as reflected in modifications in neural activity detected by the neural activity sensor.

In various aspects, the genetic algorithm modifies various parameters defining the peripheral stimulation pattern including, but not limited to, time per stimulation pattern and time per rest between peripheral stimulation patterns. In various other aspects, at least one or more parameters define the implementation of the genetic algorithm including, but not limited to, the number of peripheral stimulation patterns administered per generation, the total number of generations to implement, and parameters defining the calculation of the fitness parameter. In some aspects, the fitness parameter calculation may be influenced by the selection of measurements of neural activity to be incorporated into the fitness calculation. In these aspects, the fitness calculation may be influenced by the measurement time points included in the calculation including, but not limited to, neural activity measurements obtained prior to, during, and/or after administration of the peripheral stimulus pattern to the subject.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function that maps outputs to inputs and utilize the predictive function to generate ML outputs based on data inputs. The example inputs and example outputs of the training data may include any of the data inputs or ML outputs described above.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship.

In yet another aspect, ML methods and algorithms are directed toward reinforcement learning, which involves optimizing outputs based on feedback from a reward signal. Specifically, ML methods and algorithms directed toward reinforcement learning may receive a user-defined reward signal definition, receive data input, utilize a decision-making model to generate an ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, an ML module implements reinforcement learning in a user recommendation application. The ML module may utilize a decision-making model to generate a ranked list of options based on user information received from the user and may further receive selection data based on a user selection of one of the ranked options.

A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware, or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving media, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application-specific integrated circuits (ASICs), logic circuits, and any other circuit or processor capable of executing the functions described herein. The above examples are examples only, and are thus not intended to limit in any way the definition and/or meaning of the term "processor."

As used herein, the terms "software" and "firmware" are interchangeable and include any computer program stored in memory for execution by a processor, including RAM memory, ROM memory, EPROM memory, EEPROM memory, and non-volatile RAM (NVRAM) memory. The above memory types are examples only and are thus not limiting as to the types of memory usable for the storage of a computer program.

In one aspect, a computer program is provided, and the program is embodied on a computer-readable medium. In one aspect, the system is executed on a single computer system, without requiring a connection to a server computer. In a further aspect, the system is run in a Windows® environment (Windows is a registered trademark of Microsoft Corporation, Redmond, Washington). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes. The present aspects may enhance the functionality and functioning of computers and/or computer systems.

II. Methods of Modifying Neural States

In various aspects, the BCI system described above is used to implement a method of modifying a neural state of a subject from a baseline neural state to a target neural state by administering a series of peripheral stimulation patterns that are produced using a genetic algorithm as described above. In some aspects, the target neural states are selected based on associations of these target neural states with related effects on one or more physiological conditions of the subject. In some aspects, the target neural states are defined in terms of modifications of neural activity characterized by frequencies within one or more frequency ranges.

In some aspects, the disclosed method is used to modulate oscillations in electrical brain activity to implement a BCI-based treatment. In these aspects, the oscillations in brain activity may be classified according to known frequency ranges that are associated with various neural states, as summarized in Table 1 below.

TABLE 1

CLASSIFICATIONS OF ELECTRICAL BRAIN ACTIVITY

| CLASSIFICATION | FREQUENCY (Hz) | ASSOCIATED WITH: |
|---|---|---|
| Beta | 12-30 | Normal alert consciousness |
| Alpha | 8-12 | Relaxed, calm |
| Theta | 4-8 | Deep relaxation and meditation, mental imagery, dreams |
| Delta | <4 | Deep, dreamless sleep |

In one aspect, the BCI-implemented method may be used to modify brain activity within the delta frequency range. Theta-frequency oscillations in electrical brain activity (4-8 Hz) are associated with relaxation, mindfulness meditation. Meditation has been shown to improve chronic pain. Without being limited to any particular theory, the modification of neural states achieved using the methods described herein may result in remodeling of neural pathways according to Hebbian theory: "Cells that fire together, wire together".

In various aspects, the BCI system described above supports various operational modalities including, but not limited to, an active, user-controlled mode and a passive, computer-controlled mode. The active mode includes generating a display communicating a neural state to the subject as feedback to direct volitional modification of the subject's neural state. Over time, the subjects are trained to modify their own neural states.

Figure 13:
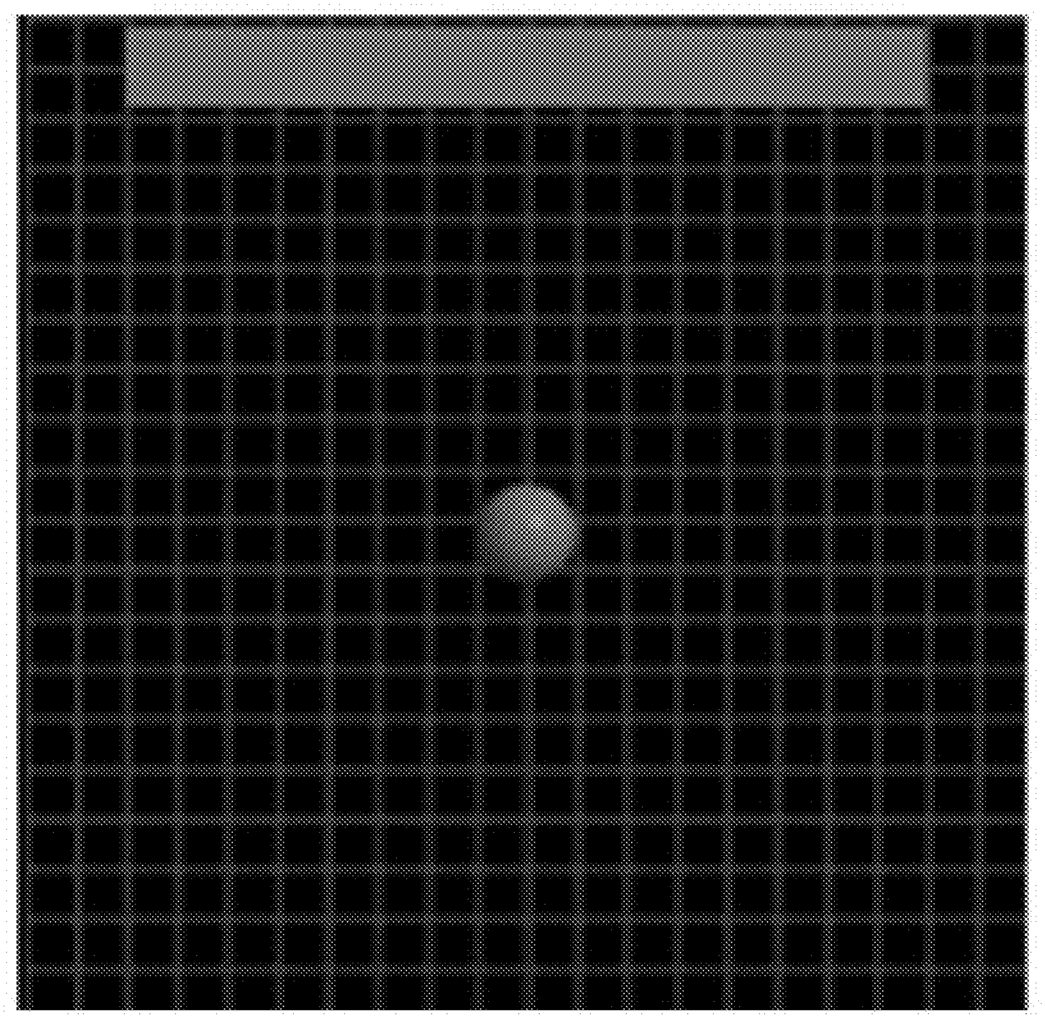
FIG. 13 is a screen capture of a visual feedback display used in the BCI system of FIG. 5 in accordance with one aspect of the disclosure.

In various aspects, the display may be a visual display in which a ball or other symbol translates upward or downward in proportion to differences between the subject's current and target neural states, such as magnitudes of neural activity within the theta frequency range may be used. By way of non-limiting example, a BCI2000 Cursor Task interface, illustrated in FIG. 13 may be used as a visual display. Within this display, a cursor moves up when the proportion of brain activity within the theta frequency range increases and down when the proportion of brain activity within the theta frequency range decreases.

Other non-limiting examples of suitable displays include other visual displays that modulate other visual elements such as alphanumerical information, and the size, shape, brightness, and/or color of a displayed object. Yet other non-limiting examples of suitable displays include auditory displays with a varying tone, volume, length, or frequency of tones.

In various other aspects, the BCI system described above supports a passive, computer-controlled mode. In these aspects, as described above, a peripheral stimulus produced using an artificial intelligence model such as the genetic algorithm described above is administered to a subject to modify the neural state of the subject.

It is to be understood that although both the active and passive modes potentially use peripheral stimulation to modify the neural state of the subject, a fundamental difference exists as to how the peripheral stimulation is utilized. When operating the BCI system in the active mode, a peripheral stimulation is generated in proportion to the current neural state of the subject and is used as feedback by the subject to actively modify the subject's neural state by volitional means. When operating the BCI system in the passive mode, a peripheral stimulation is generated according to an artificial intelligence model such as a genetic algorithm, which modifies peripheral stimulation patterns based on the analysis of modifications of the subject's neural states induced by the administration of the peripheral stimulation patterns. When operating in the active mode, the subject must actively modify the neural state, and the efficacy of the treatment may be attenuated by subject-related factors such as subject fatigue, subject attention, and/or subject effort.

When operating in the passive mode, modifications of peripheral stimulation patterns are designed using an artificial intelligence model to transform the subject's baseline neural state to a target neural state without any volitional input required from the subject. Consequently, modification of the subject's neural state using the BCI system operating in the active mode as described herein obviates many of the subject-related limitations of similar modifications accomplished using the BCI system in the active mode. Further, without being limited to any particular theory, at least some neural states are not under volitional control by the subject, and therefore at least a portion of target neural states may be achieved only by operating the BCI system in the passive mode.

By way of non-limiting example, a method for transforming a neural state of a subject from a baseline neural state to a target neural state is illustrated in FIG. 14. The method includes providing a BCI system that includes a computing device operatively coupled to a neural activity sensor and a peripheral stimulation device as illustrated, for example, in FIGS. 5 and 26. Referring again to FIG. 14, the method further includes obtaining a plurality of baseline neural activity measurements using the neural activity sensor. The computing device receives the plurality of baseline neural activity measurements and processes these measurements to determine the baseline neural state of the subject.

The method further includes producing an initial peripheral stimulation pattern as described above and illustrated in FIG. 15. The initial peripheral stimulation pattern, which includes randomly generated activation patterns of the individual motor disc elements, are used to operate the peripheral stimulation device and is followed by a period of rest. The method further includes obtaining a plurality of modified neural activity measurements using the neural activity sensor during and/or after administration of the peripheral stimulation pattern. Using an artificial intelligence model (i.e. a genetic algorithm), the method further includes generating the subject's modified neural state induced by the administration of the peripheral stimulation pattern. In addition, the genetic algorithm modifies the peripheral stimulation pattern based on features extracted from the plurality of modified neural activity measurements as described above.

In various aspects, the method includes iteratively modifies the peripheral stimulation patterns and monitors modifications in the subject's neural state until the subject's neural state is matched to the target neural state.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

The non-limiting examples are provided below to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

EXAMPLES

The following examples are provided to illustrate various aspects of the disclosure.

Example 1: Effect of Frequency of Tactile Stimulation on Electrophysiological Responses To assess the effect of tactile stimulations on electrophysiological responses, the following experiments were conducted.

A BRI system similar to the system illustrated in FIG. 26 and as described herein was used to conduct these experiments. A wearable EEG dry electrode array containing 24 electrodes distributed over the scalp of the subject and configured to record EEG signals at a variety of regions, including a frontal pole (Fp) region, a central (C) region, a parietal (P) region, an occipital (O) region, and a temporal (T) region. The peripheral stimulation device used in these experiments was a tactile stimulation device that included two arrays of motor discs similar to the arrays shown illustrated in FIG. 11. The arrays were configured to administer a tactile stimulus pattern delivered at a characteristic stimulus frequency.

The wearable EEG electrode array and peripheral stimulation device were fitted to a subject. Peripheral stimulation patterns were administered to the subject at stimulation frequencies of 5 Hz, 7 Hz, 11 Hz, and 85 Hz using the peripheral stimulation device while recording brain electrophysiological activity. The electrophysiological measurements were analyzed as described herein.

Figure 21A:
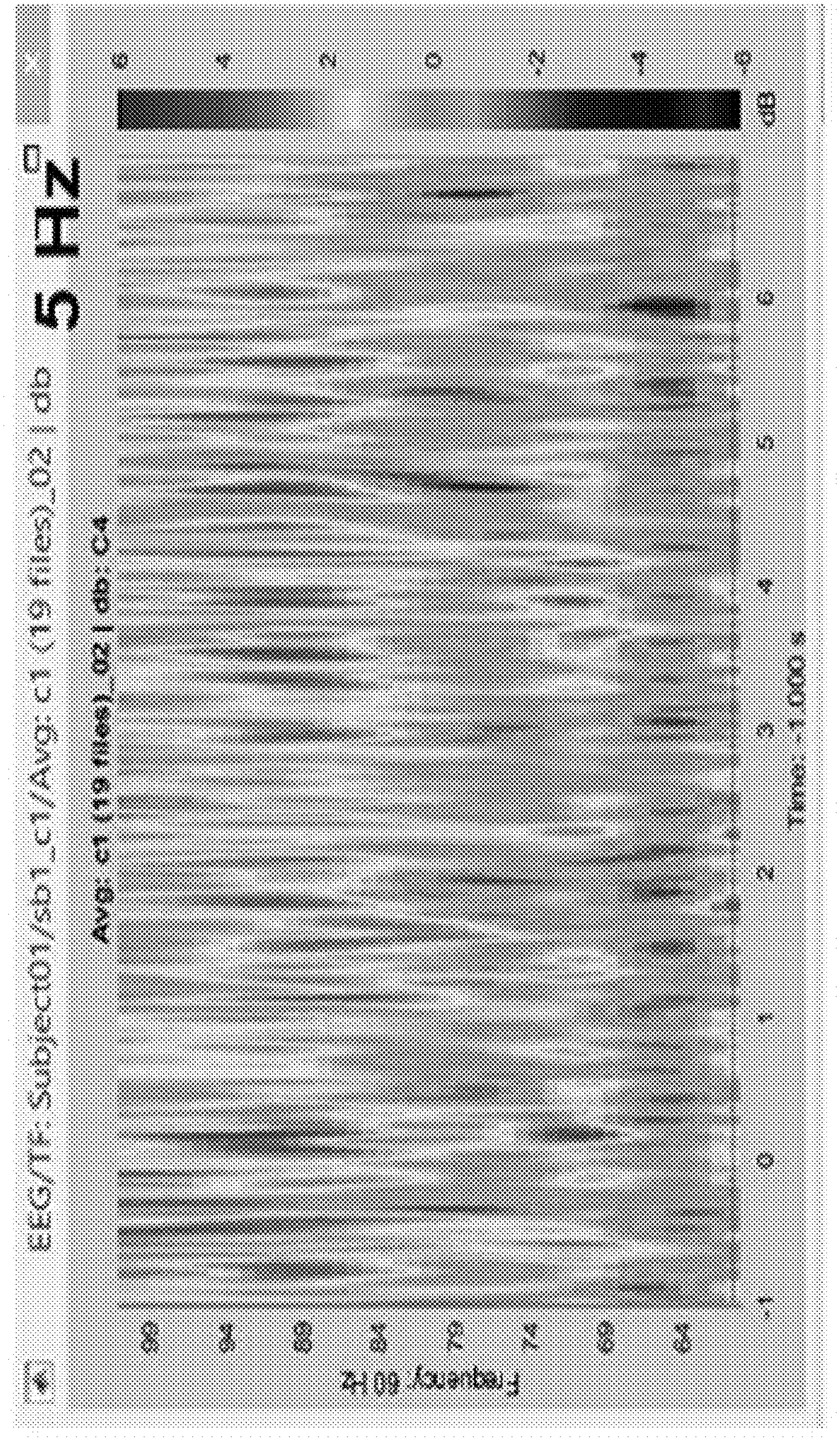
FIG. 21A is a spectrogram summarizing higher-frequency electrophysiological responses to tactile peripheral stimulation patterns administered at a frequency of 5 Hz.
Figure 21B:
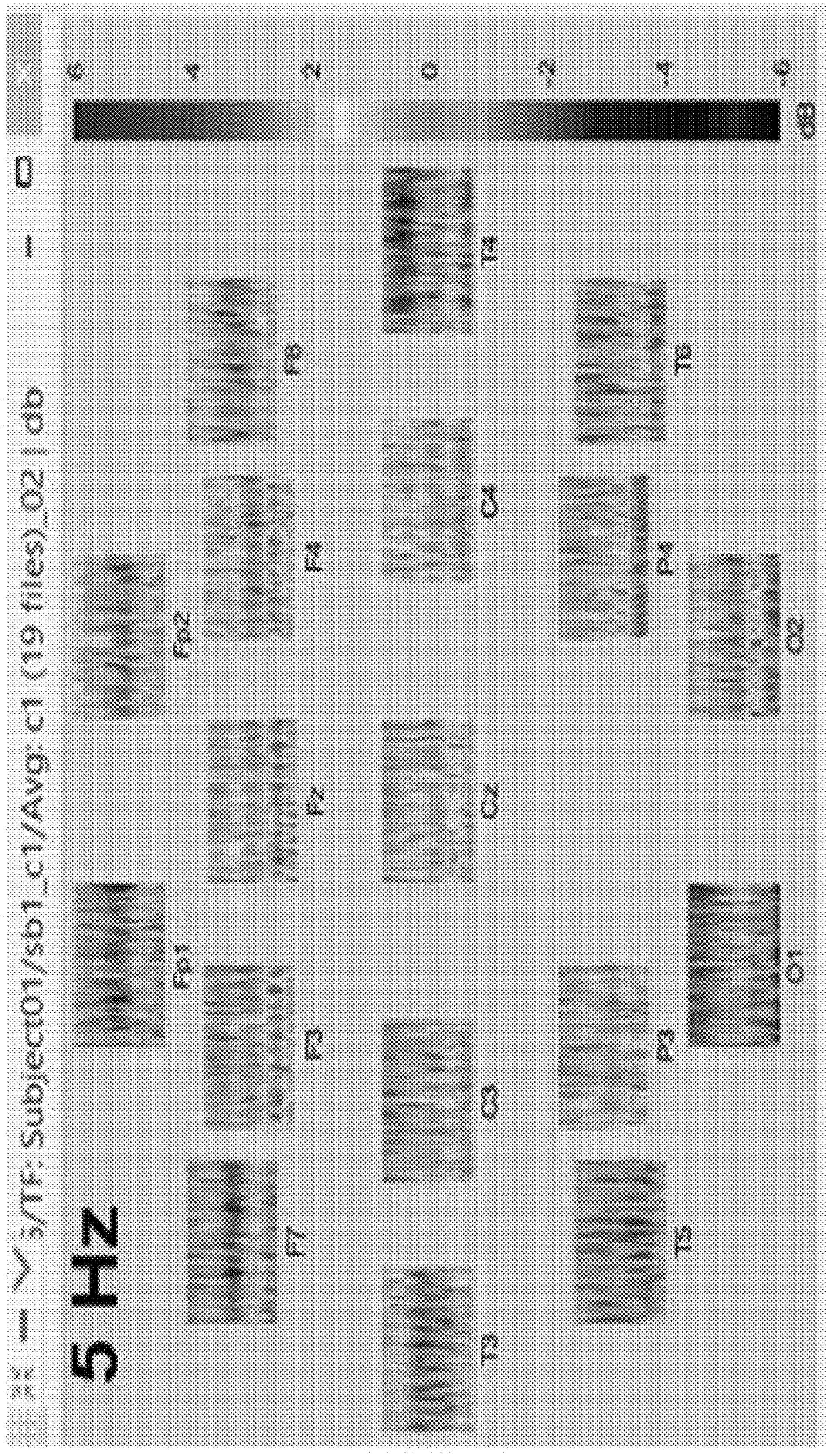
FIG. 21B contains regional spectrograms showing local higher-frequency electrophysiological responses to tactile peripheral stimulation patterns administered at a frequency of 5 Hz.
Figure 21C:
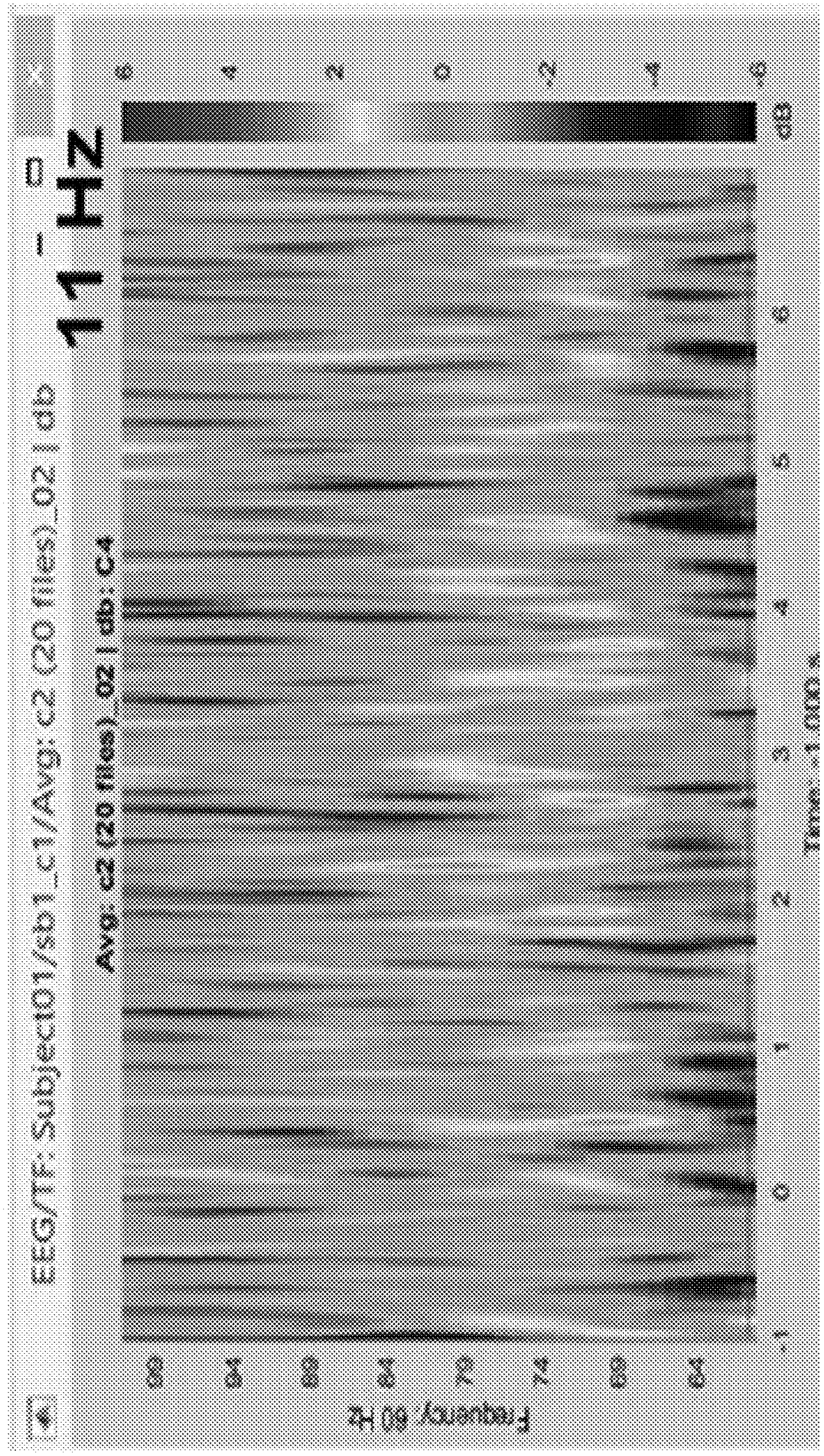
FIG. 21C is a spectrogram summarizing higher-frequency electrophysiological responses to tactile peripheral stimulation patterns administered at a frequency of 11 Hz.
Figure 21D:
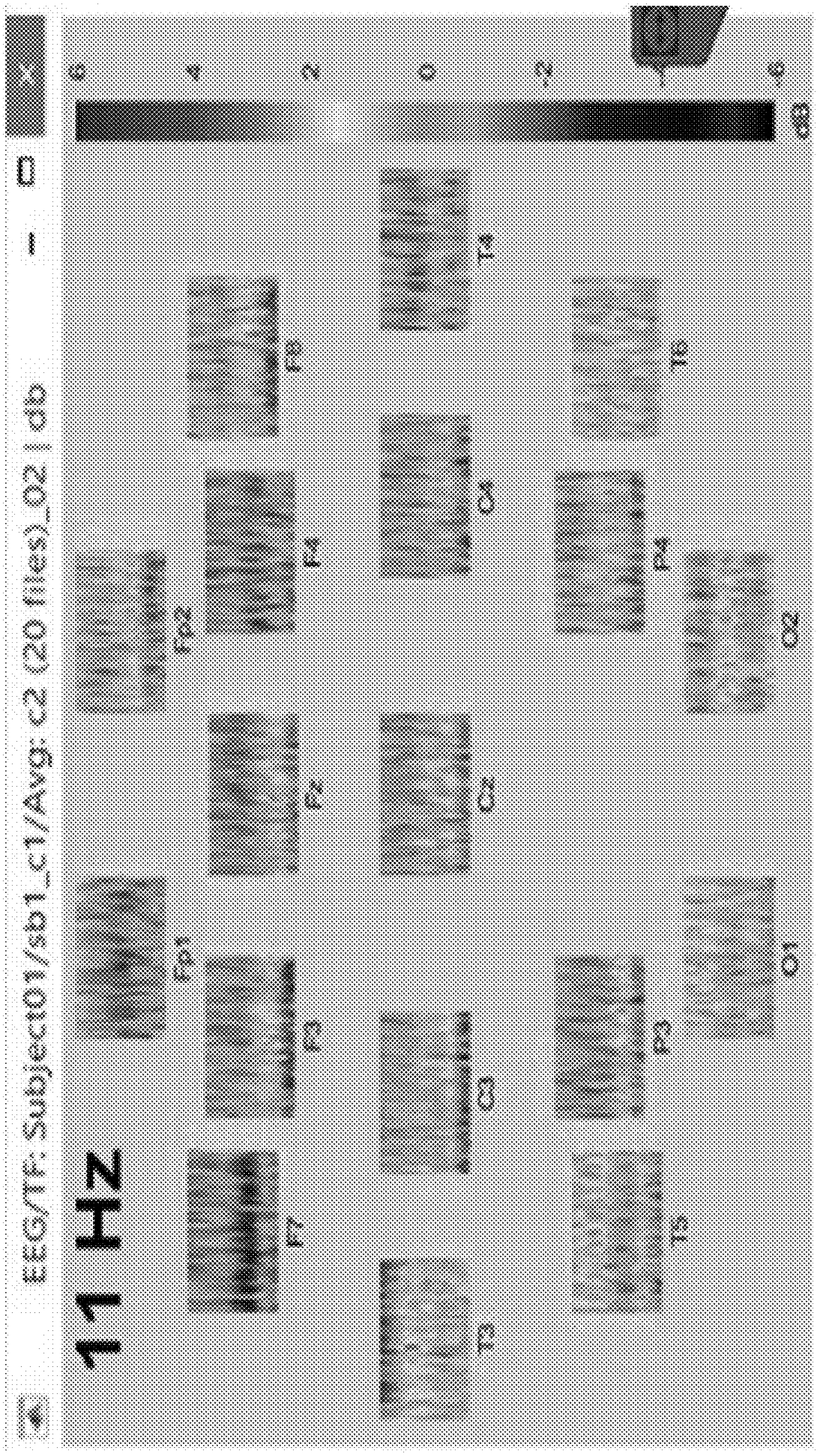
FIG. 21D contains regional spectrograms showing local higher-frequency electrophysiological responses to tactile peripheral stimulation patterns administered at a frequency of 11 Hz.
Figure 25A:
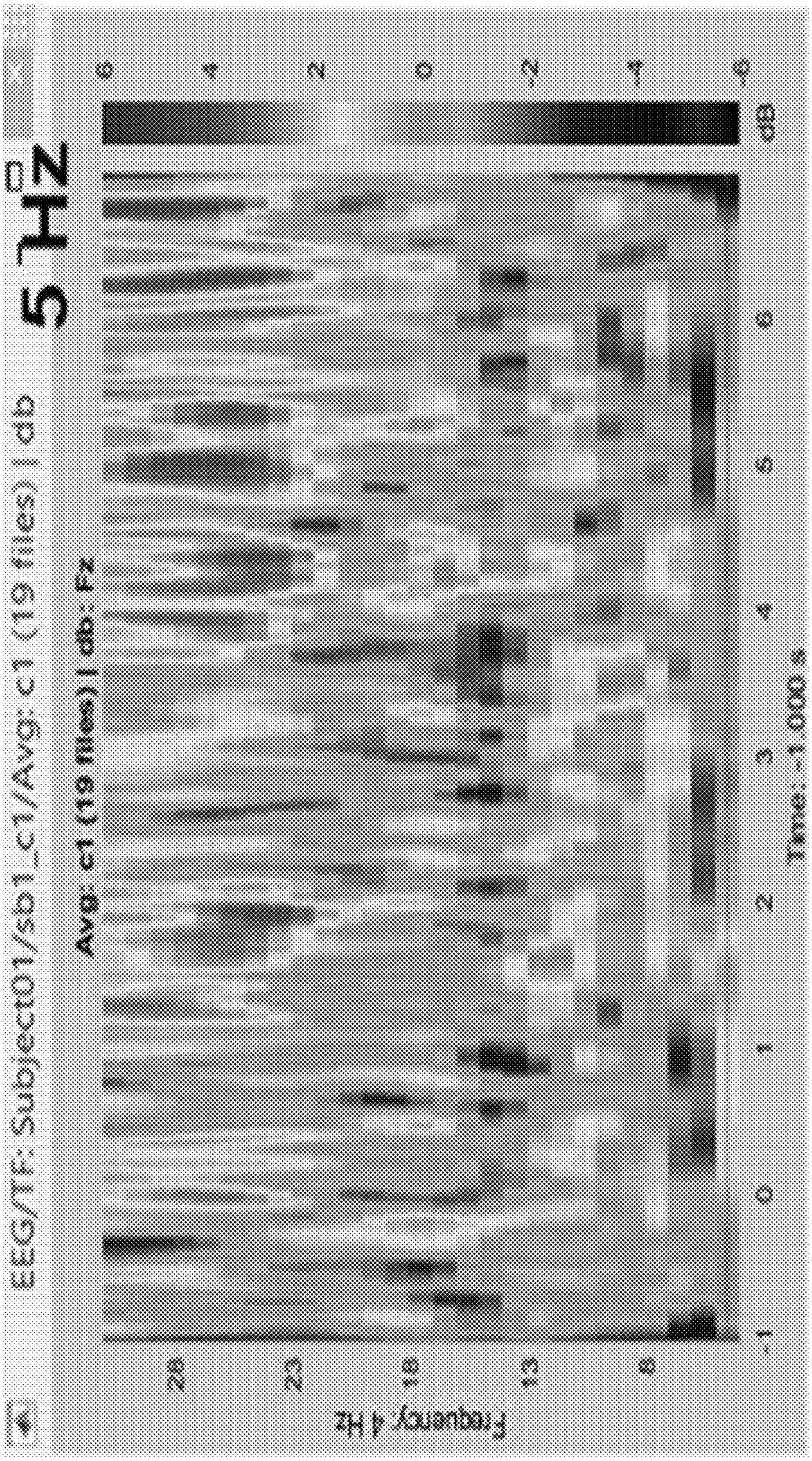
FIG. 25A is a spectrogram summarizing lower-frequency electrophysiological responses to tactile peripheral stimulation patterns administered at a frequency of 5 Hz.
Figure 25B:
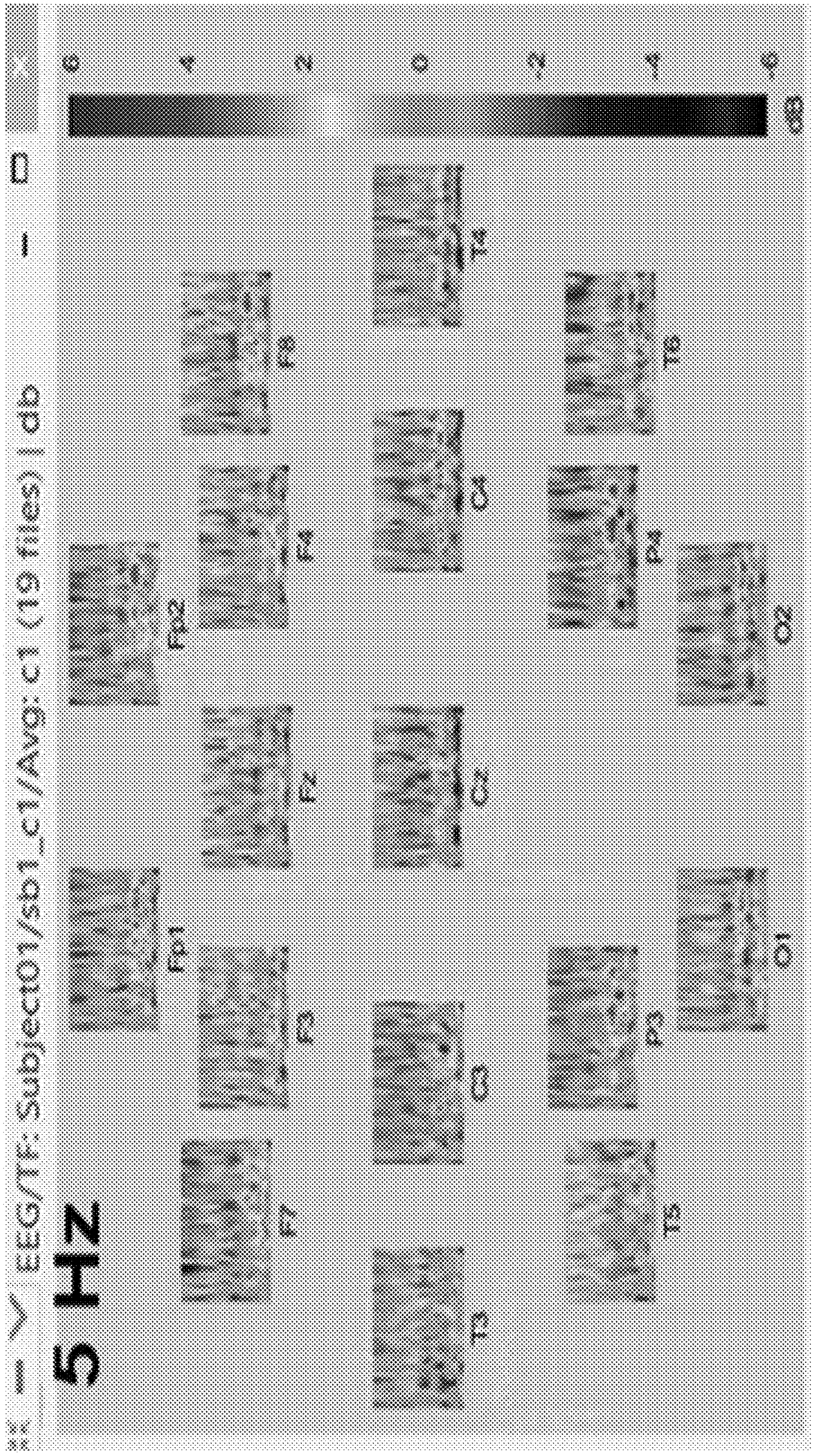
FIG. 25B contains regional spectrograms showing local lower-frequency electrophysiological responses to tactile peripheral stimulation patterns administered at a frequency of 5 Hz.

FIG. 25A and FIG. 25B are maps of average and local changes, respectively, in higher-frequency electrophysiological activity due to the administration of tactile stimulation patterns at a frequency of 5 Hz. FIG. 21C and FIG. 21D are maps of average and local changes, respectively, in higher-frequency electrophysiological activity due to the administration of tactile stimulation patterns at a frequency of 11 Hz. Higher-frequency gamma rhythm power increases were observed when the subject was stimulated at 5 Hz, as illustrated in FIG. 21A. The magnitude of higher-frequency gamma power increase varied over different brain regions, as illustrated in FIG. 21B. Peripheral stimulation at 11 Hz did not induce any changes in higher-frequency gamma rhythm power, as summarized in FIG. 21C and FIG. 21D.

Figure 25C:
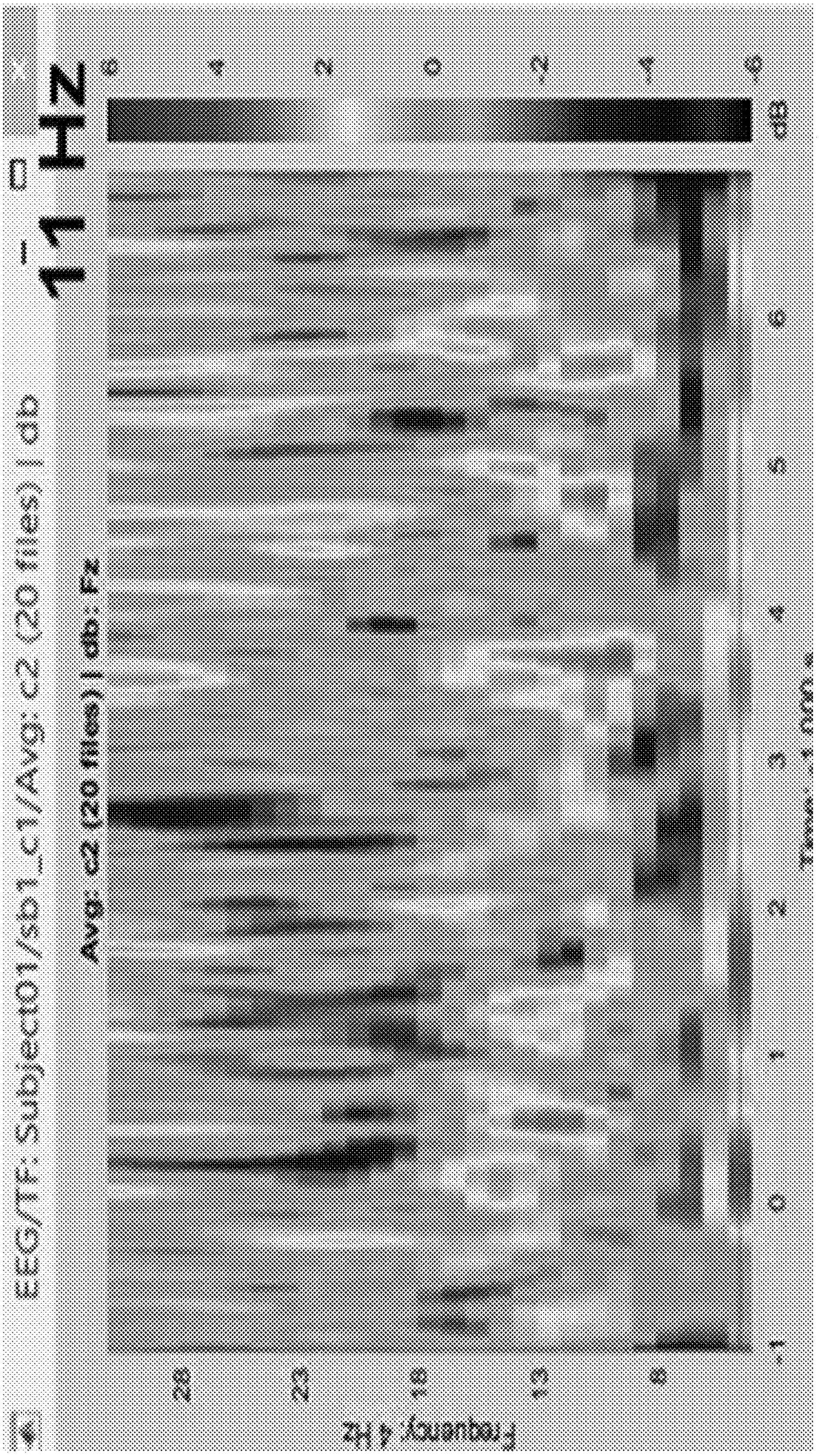
FIG. 25C is a spectrogram summarizing lower-frequency electrophysiological responses to tactile peripheral stimulation patterns administered at a frequency of 11 Hz.
Figure 25D:
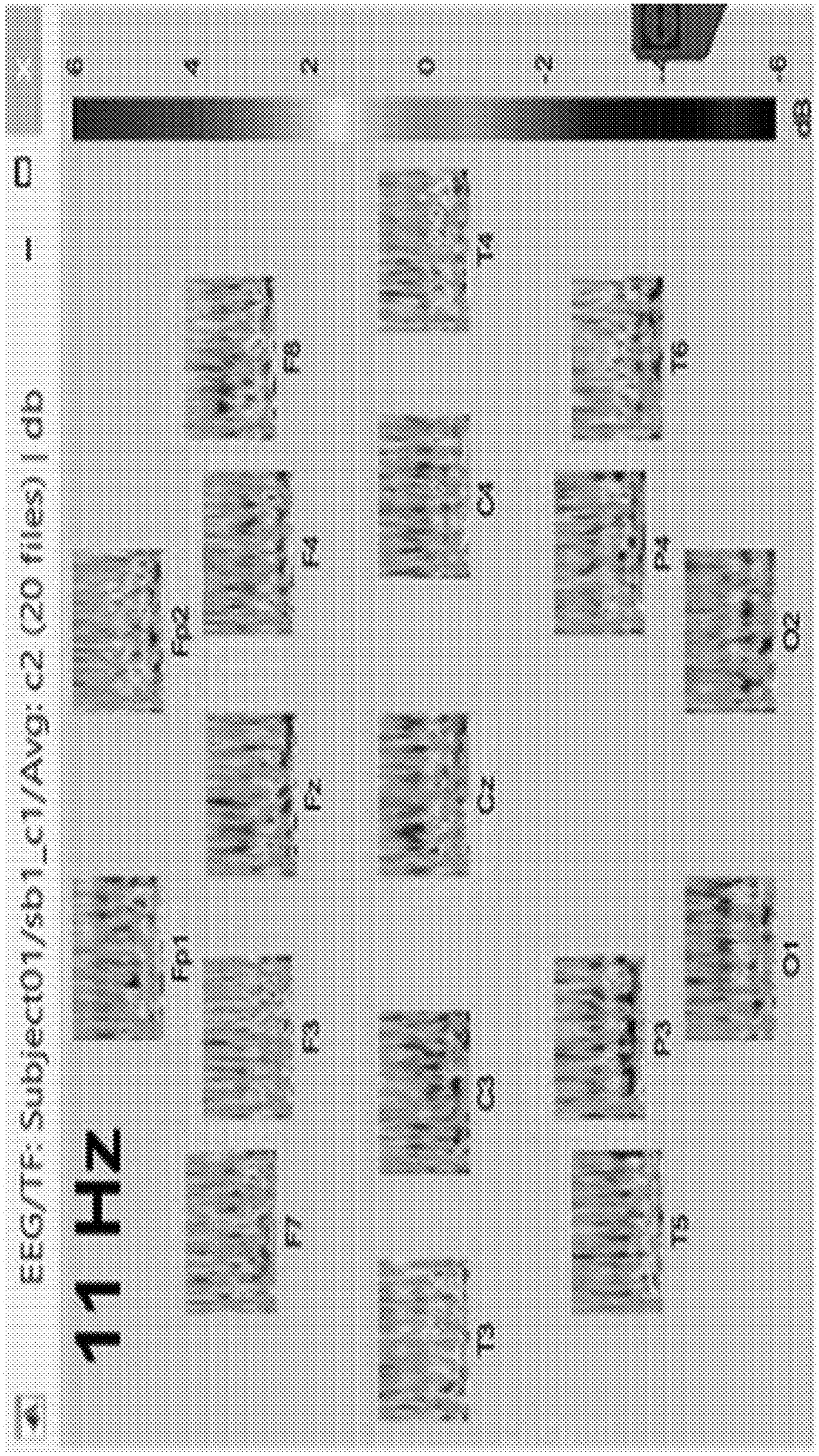
FIG. 25D contains regional spectrograms showing local lower-frequency electrophysiological responses to tactile peripheral stimulation patterns administered at a frequency of 11 Hz.

FIG. 25A and FIG. 25B are maps of average and local changes, respectively, in lower-frequency electrophysiological activity due to the administration of tactile stimulation patterns at a frequency of 5 Hz. FIG. 25C and FIG. 25D are maps of average and local changes, respectively, in lower-frequency electrophysiological activity due to the administration of tactile stimulation patterns at a frequency of 11 Hz. Lower-frequency power increases were observed when the subject was stimulated at 5 Hz, as illustrated in FIG. 25A. The magnitude of lower-frequency power increase varied over different brain regions, as illustrated in FIG. 25B. Peripheral stimulation at 11 Hz did not induce any changes in lower-frequency power, as summarized in FIG. 25C and FIG. 25D.

Figure 22A:
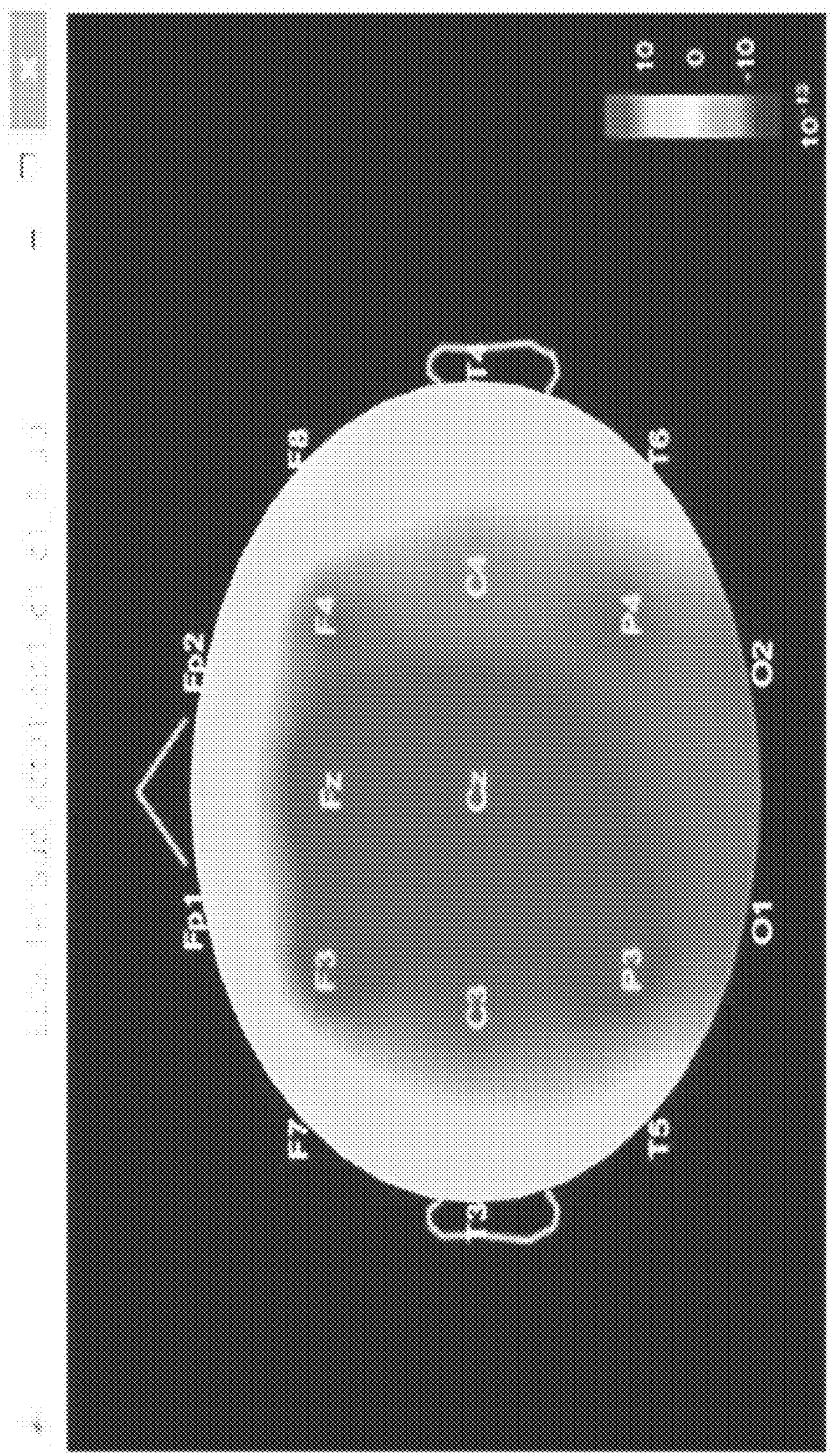
FIG. 22A is a topographic map of low-frequency electrophysiological responses to tactile peripheral stimulation patterns administered at a frequency of 5 Hz.
Figure 22B:
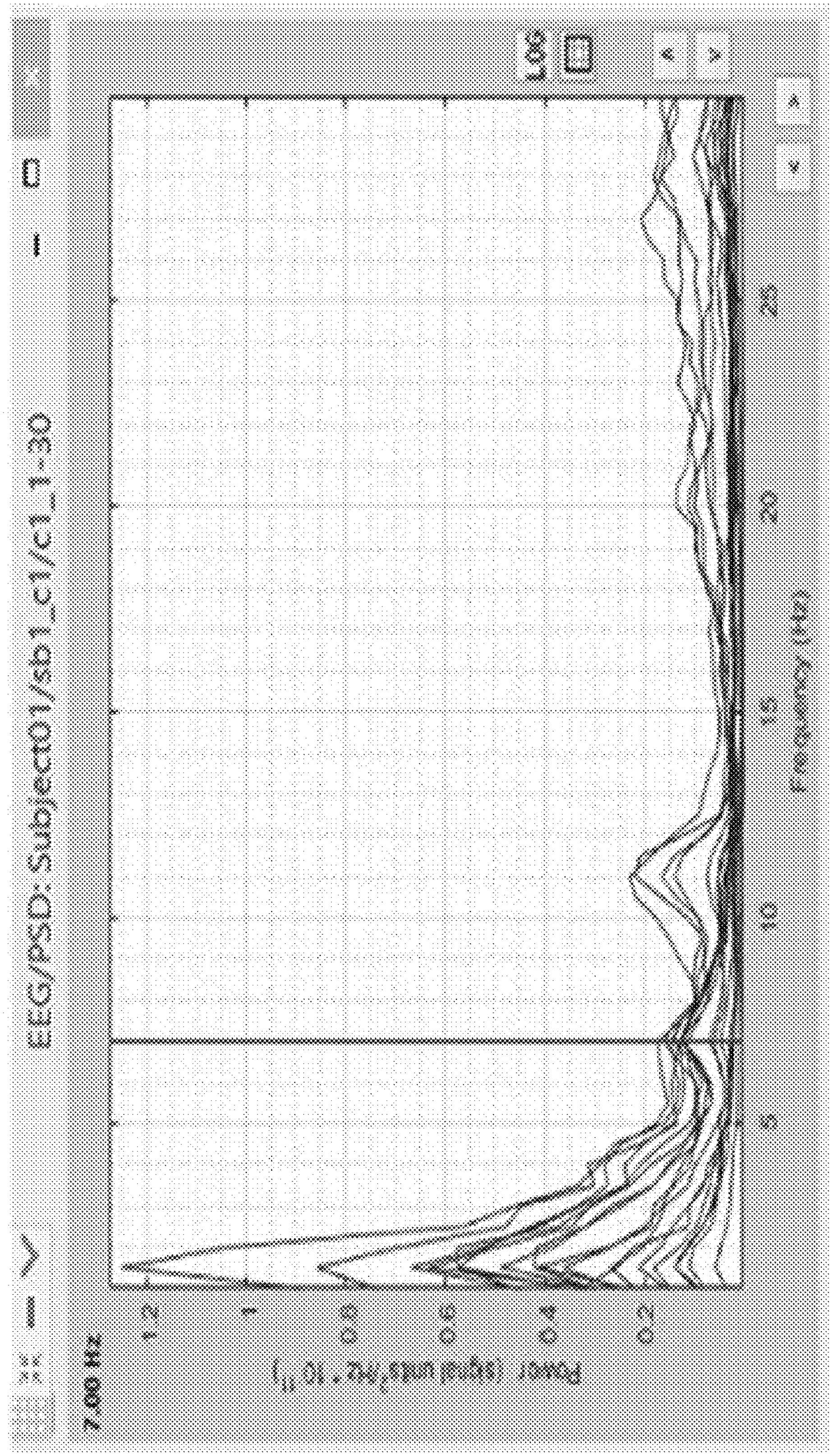
FIG. 22B is a series of spectral power plots from individual electrodes summarizing low-frequency electrophysiological responses to tactile peripheral stimulation patterns administered at a frequency of 5 Hz.
Figure 22C:
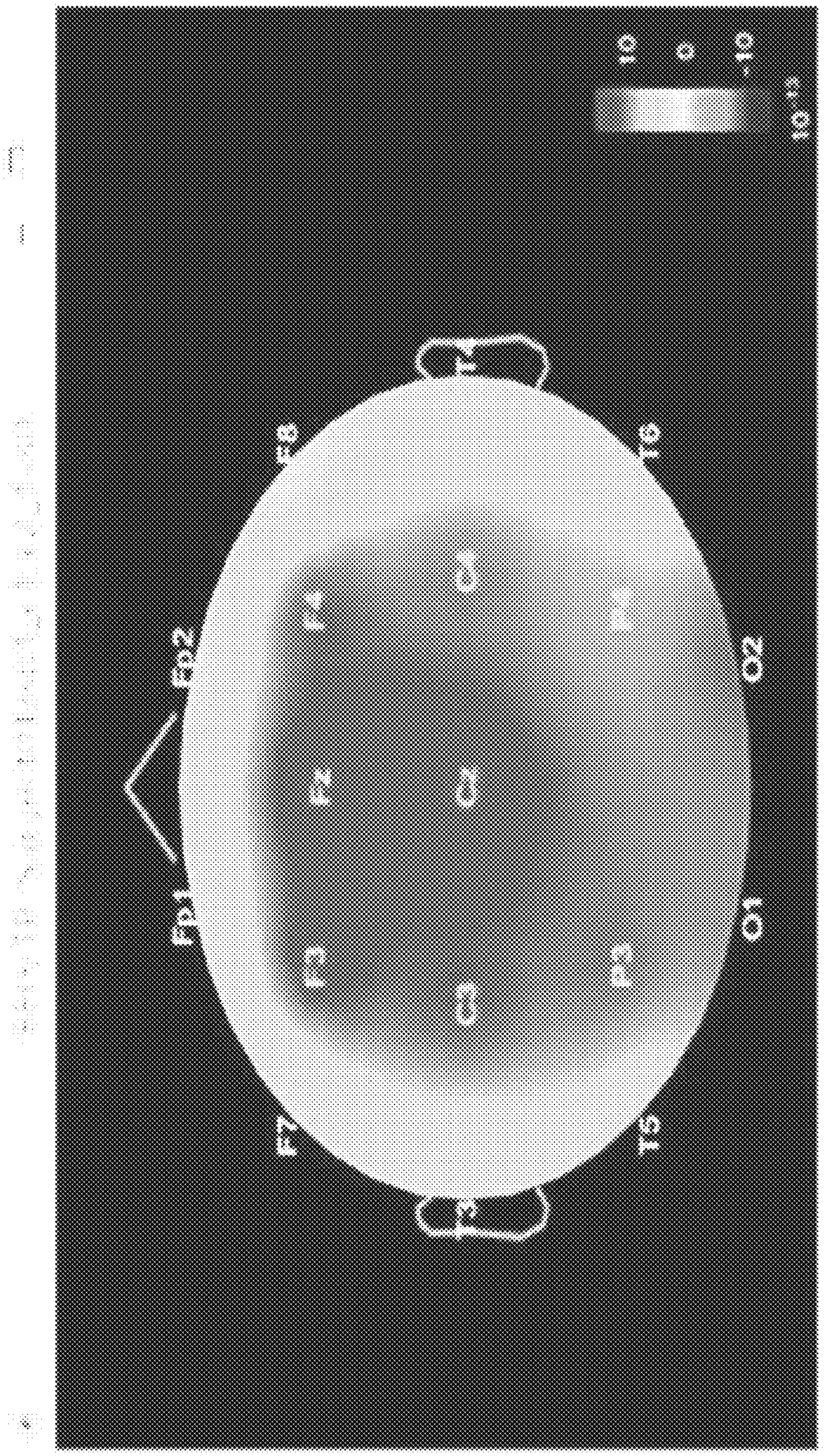
FIG. 22C is a topographic map of low-frequency electrophysiological responses to tactile peripheral stimulation patterns administered at a frequency of 11 Hz.
Figure 22D:
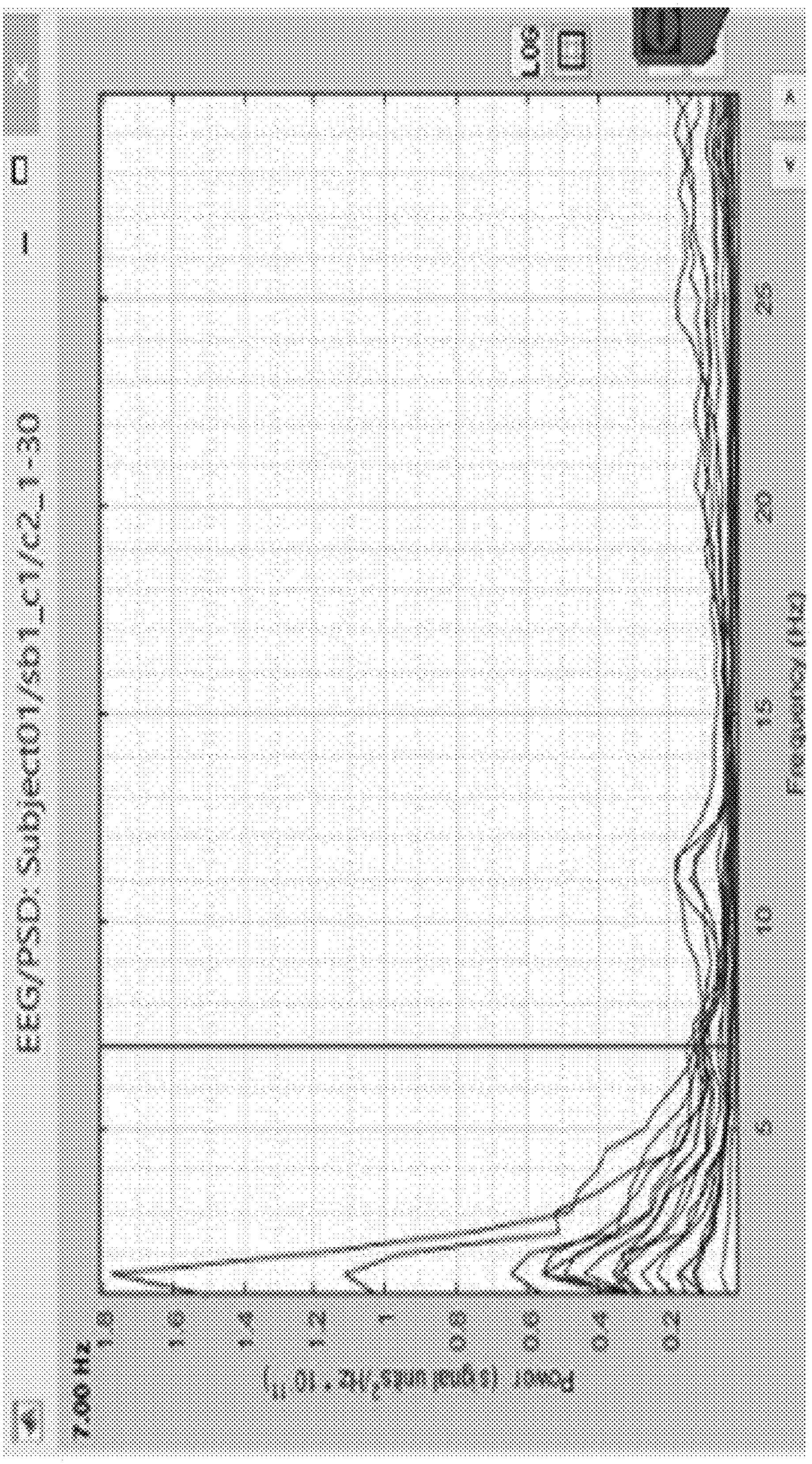
FIG. 22D is a series of spectral power plots from individual electrodes summarizing low-frequency electrophysiological responses to peripheral stimulation patterns administered at a frequency of 11 Hz.
Figure 23A:
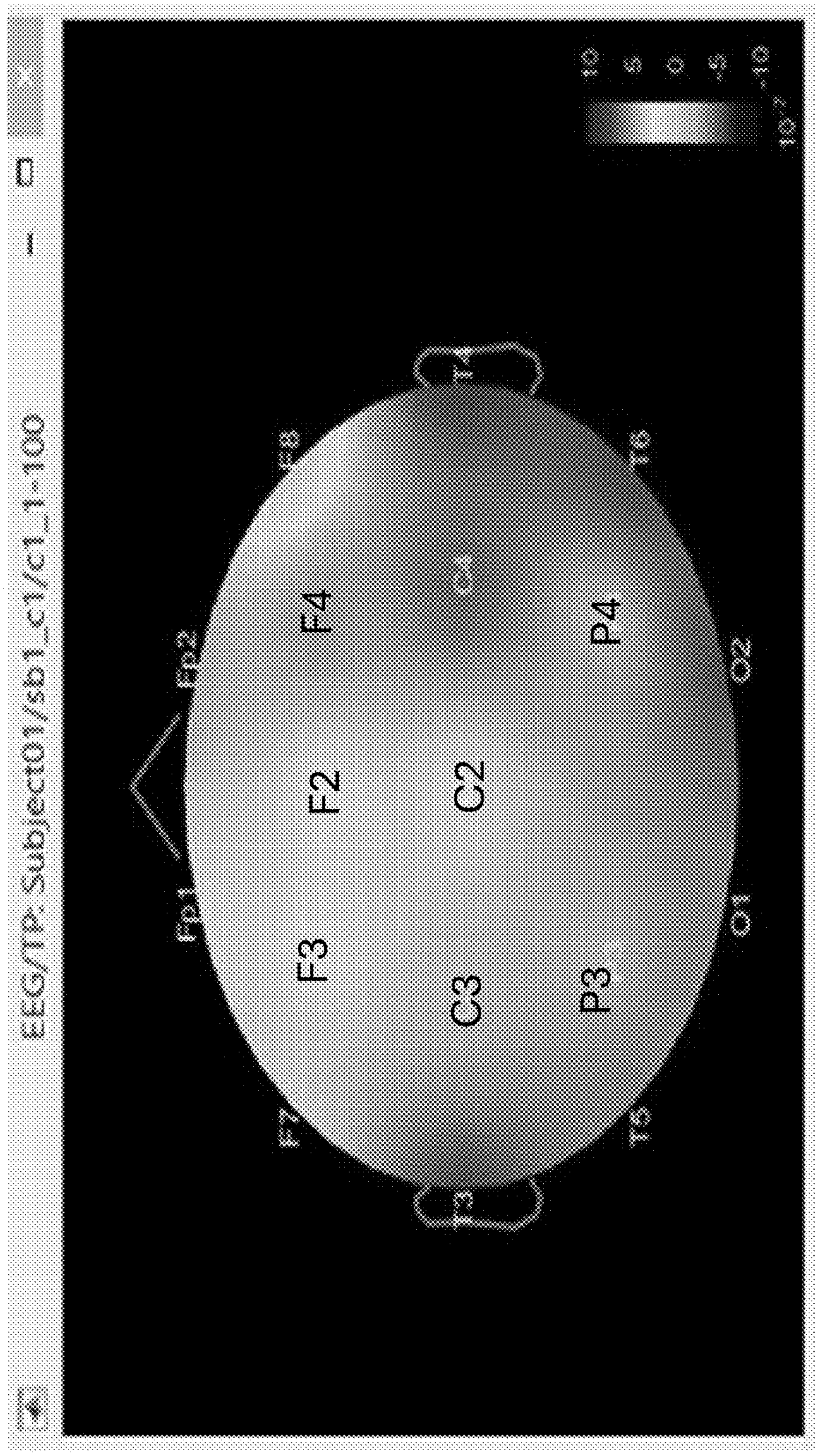
FIG. 23A is a topographic map of higher-frequency electrophysiological responses to tactile peripheral stimulation patterns administered at a frequency of 5 Hz.
Figure 23B:
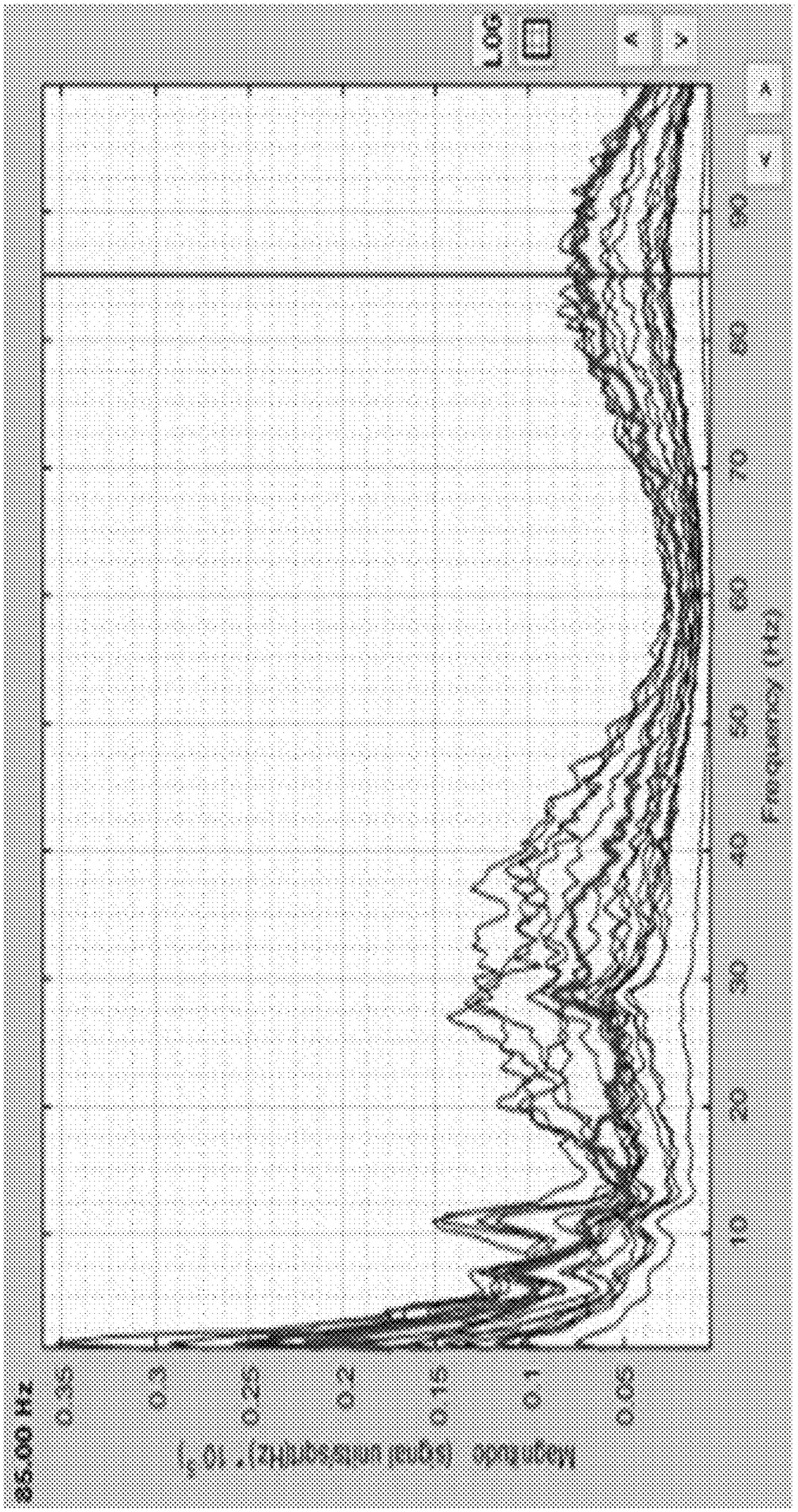
FIG. 23B is a series of spectral power plots from individual electrodes summarizing higher-frequency electrophysiological responses to tactile peripheral stimulation patterns administered at a frequency of 5 Hz.
Figure 23C:
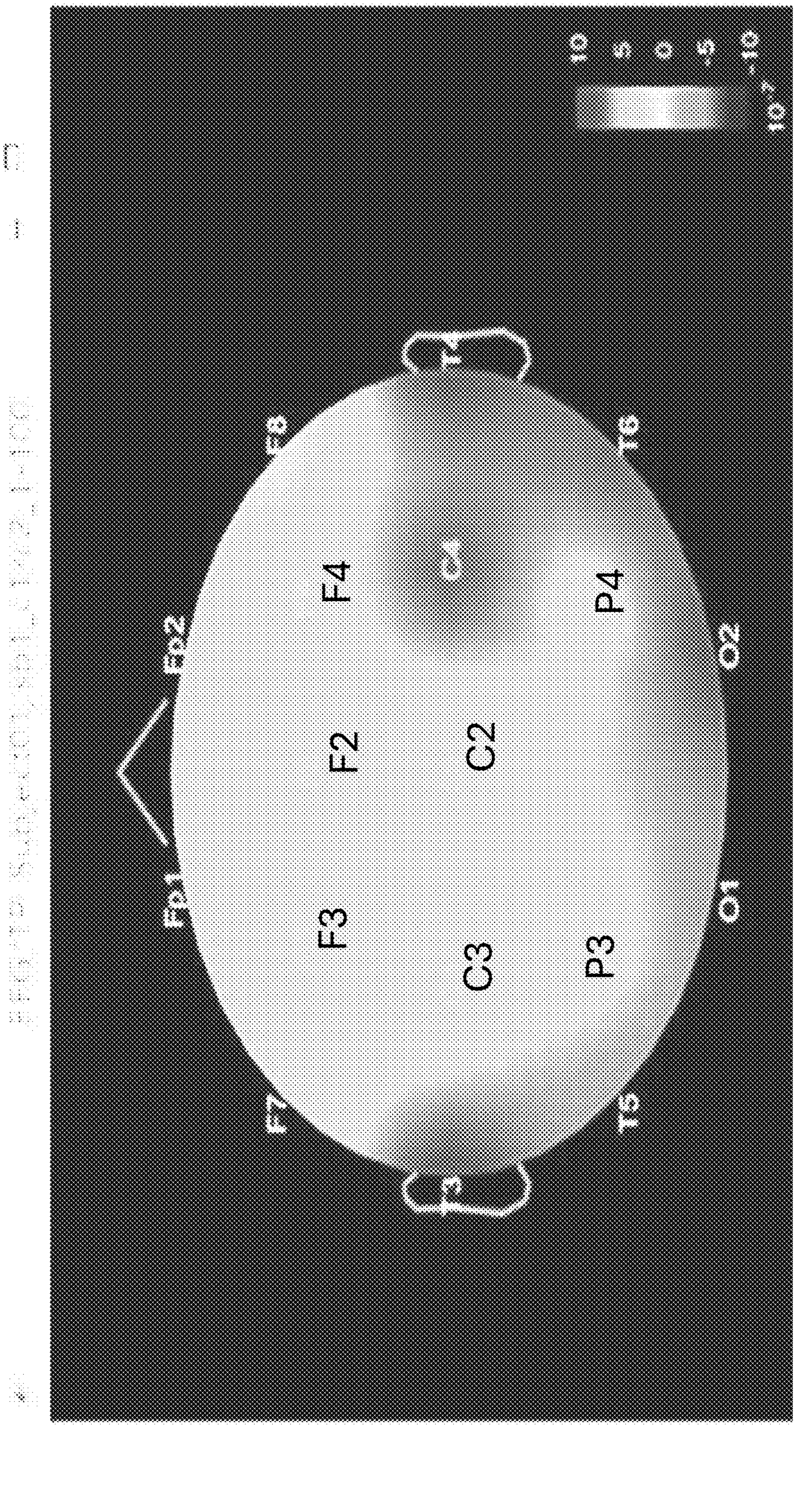
FIG. 23C is a topographic map of higher-frequency electrophysiological responses to tactile peripheral stimulation patterns administered at a frequency of 11 Hz.
Figure 23D:
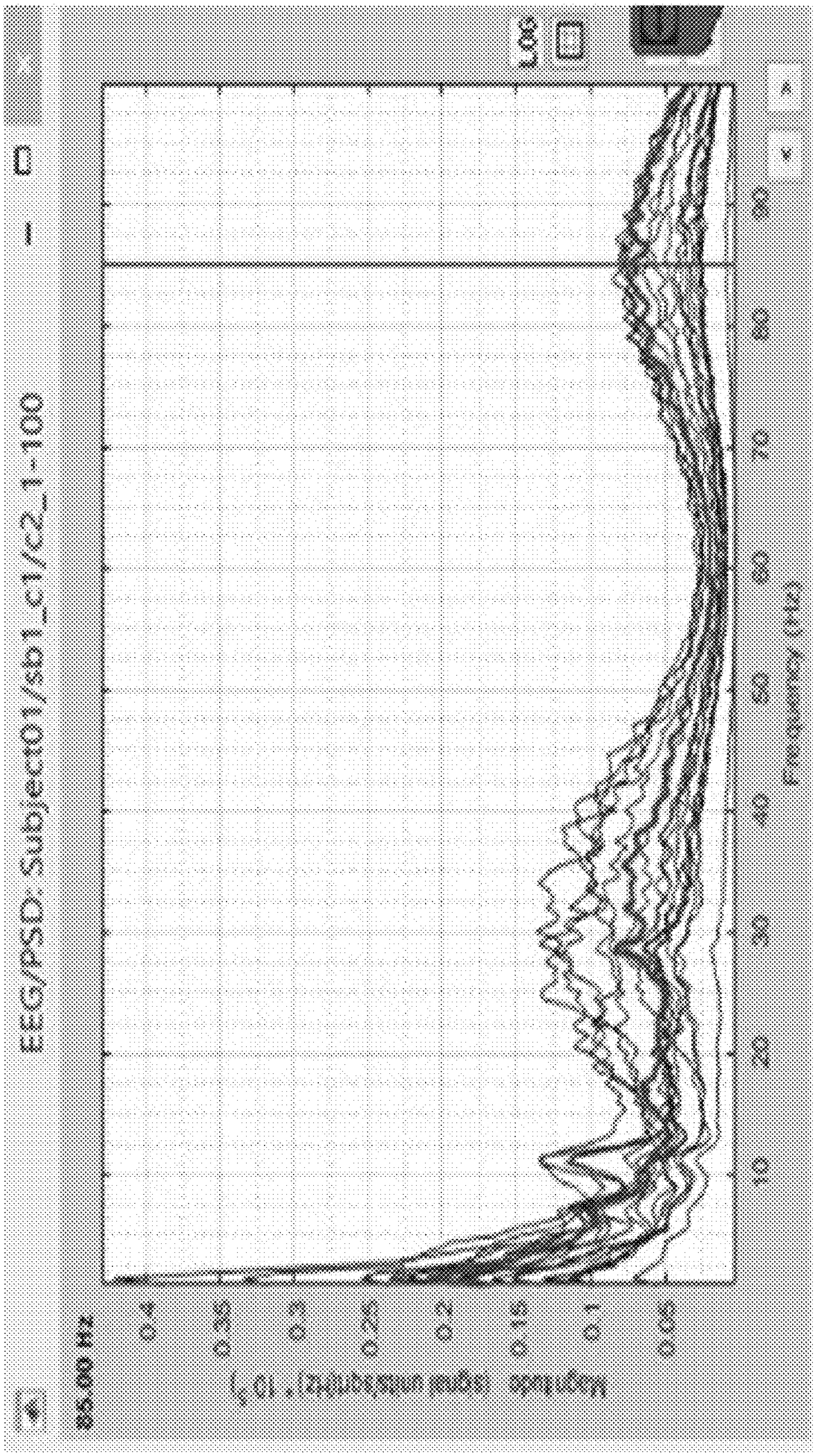
FIG. 23D is a series of spectral power plots from individual electrodes summarizing higher-frequency electrophysiological responses to tactile peripheral stimulation patterns administered at a frequency of 11 Hz.
Figure 24A:
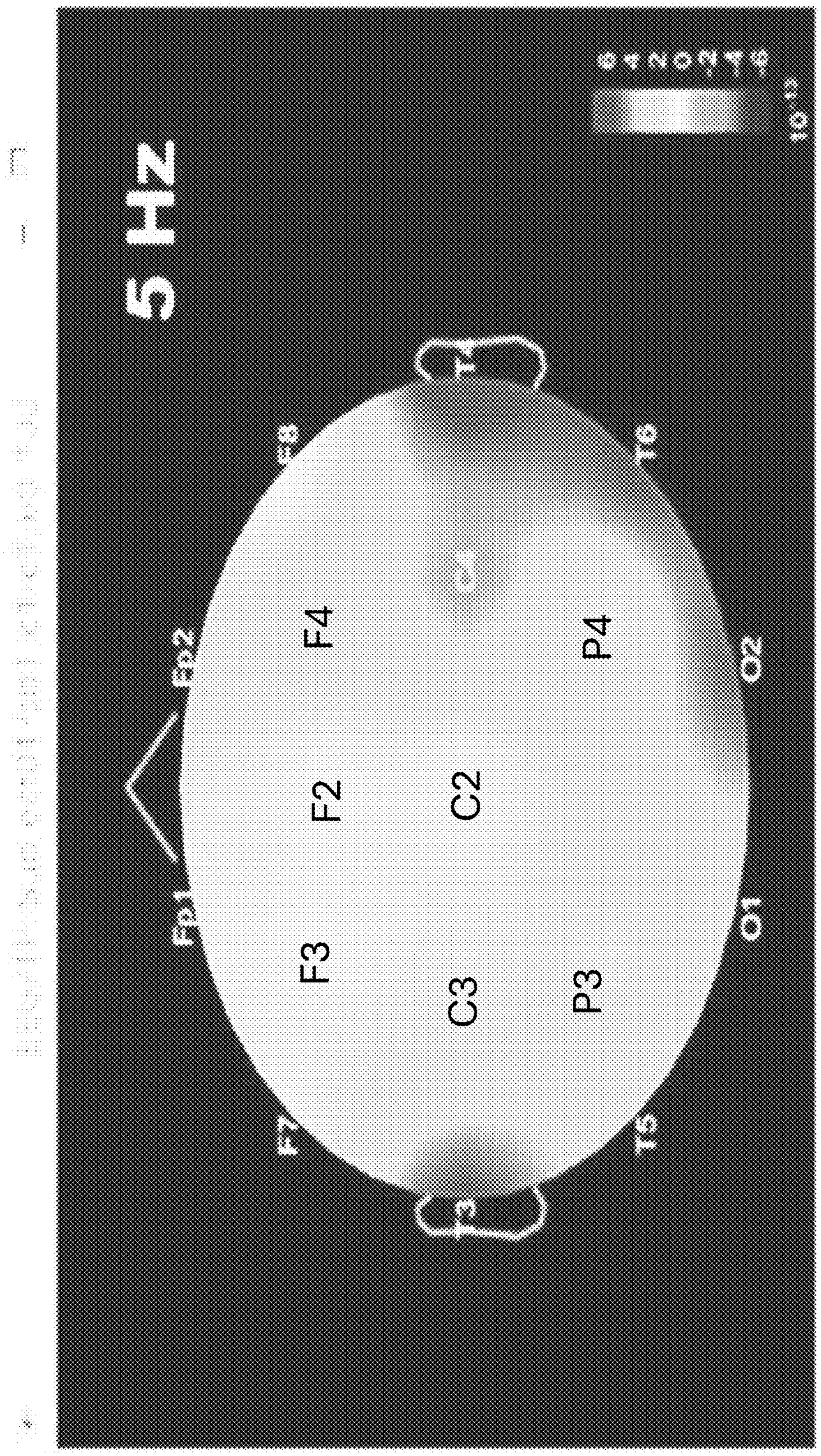
FIG. 24A is a topographic map of higher-frequency electrophysiological responses to tactile peripheral stimulation patterns administered at a frequency of 5 Hz.
Figure 24B:
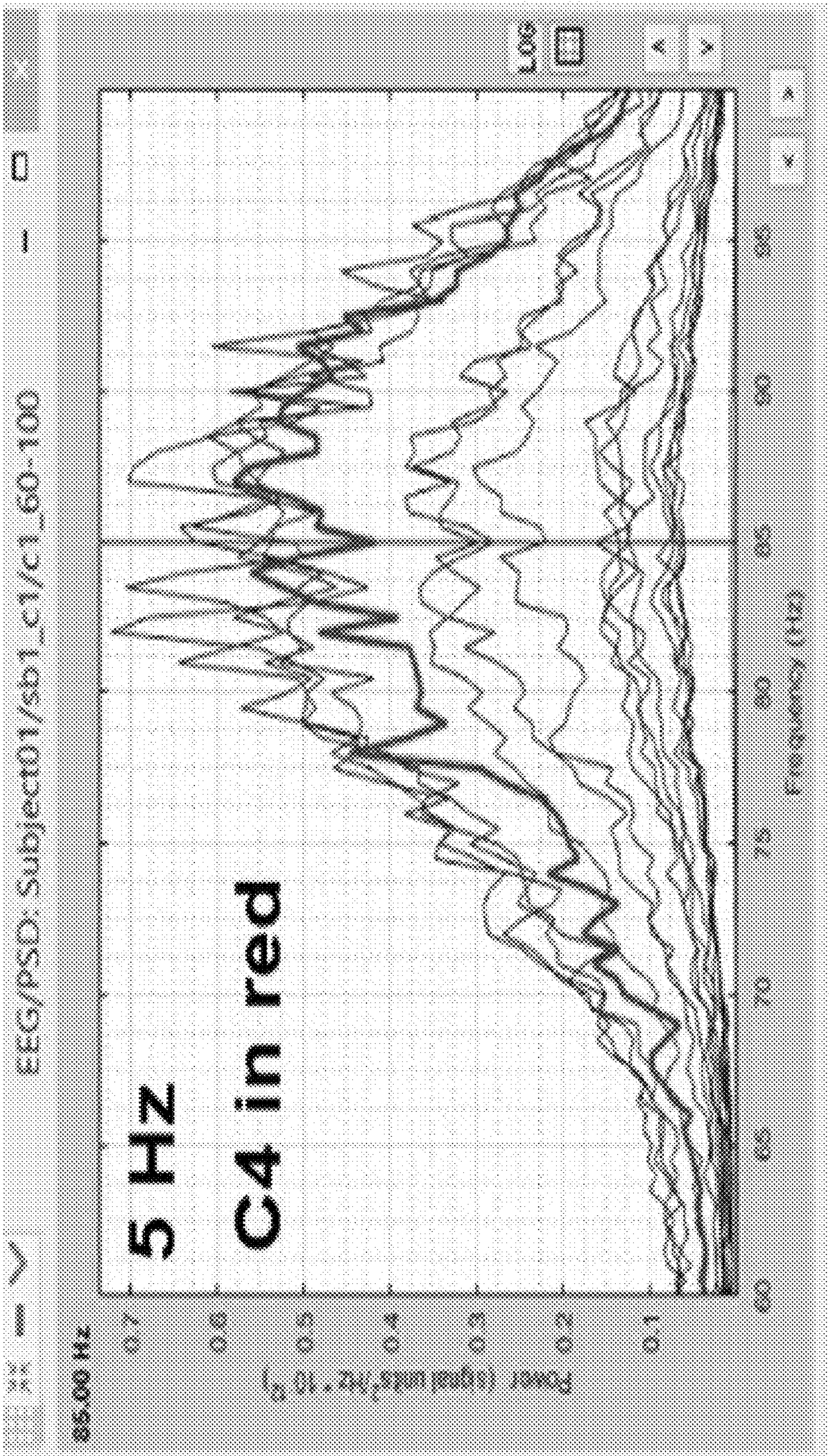
FIG. 24B is a series of spectral power plots from individual electrodes summarizing higher-frequency electrophysiological responses to tactile peripheral stimulation patterns administered at a frequency of 5 Hz.
Figure 24C:
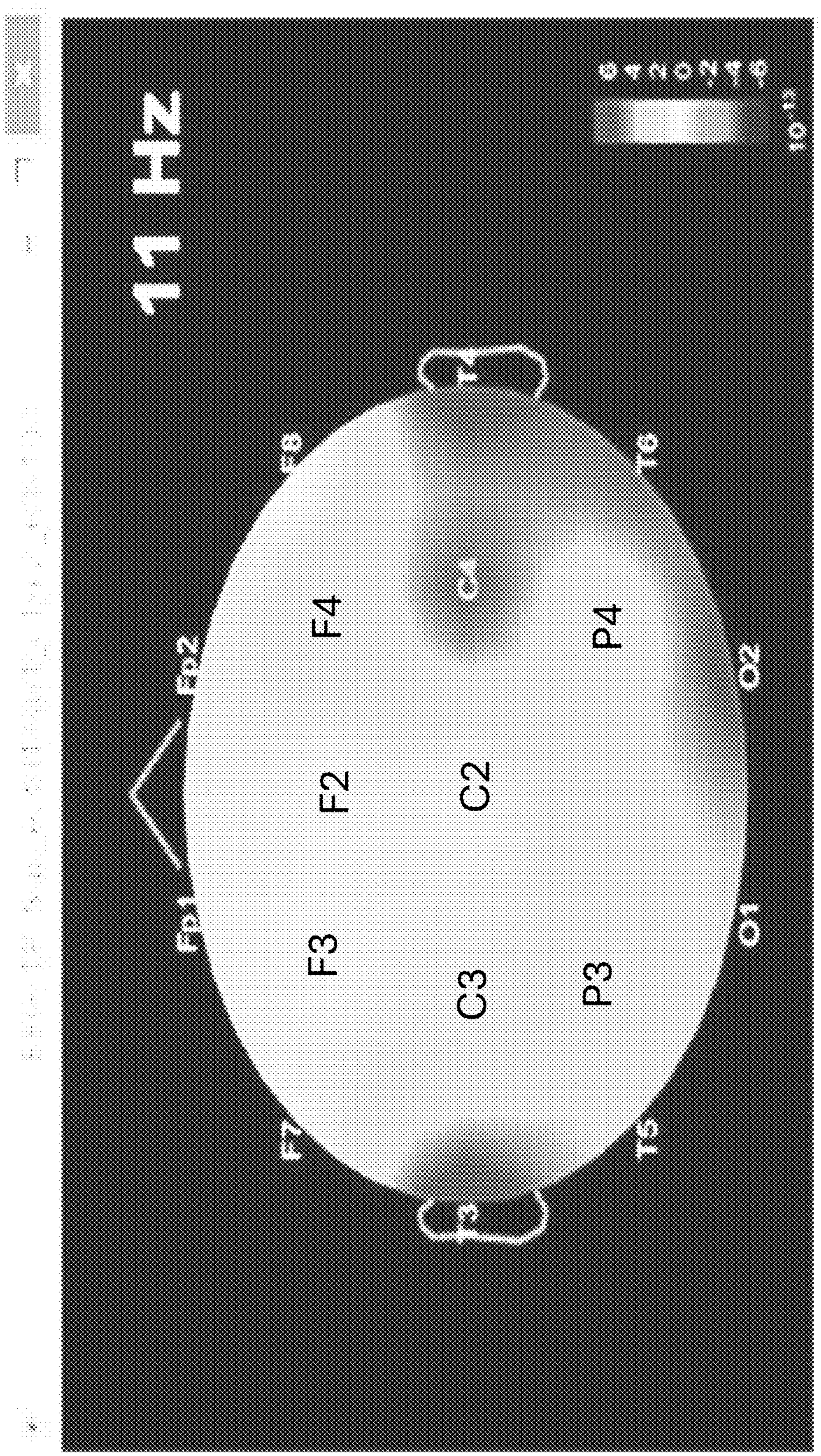
FIG. 24C is a topographic map of higher-frequency electrophysiological responses to tactile peripheral stimulation patterns administered at a frequency of 11 Hz.
Figure 24D:
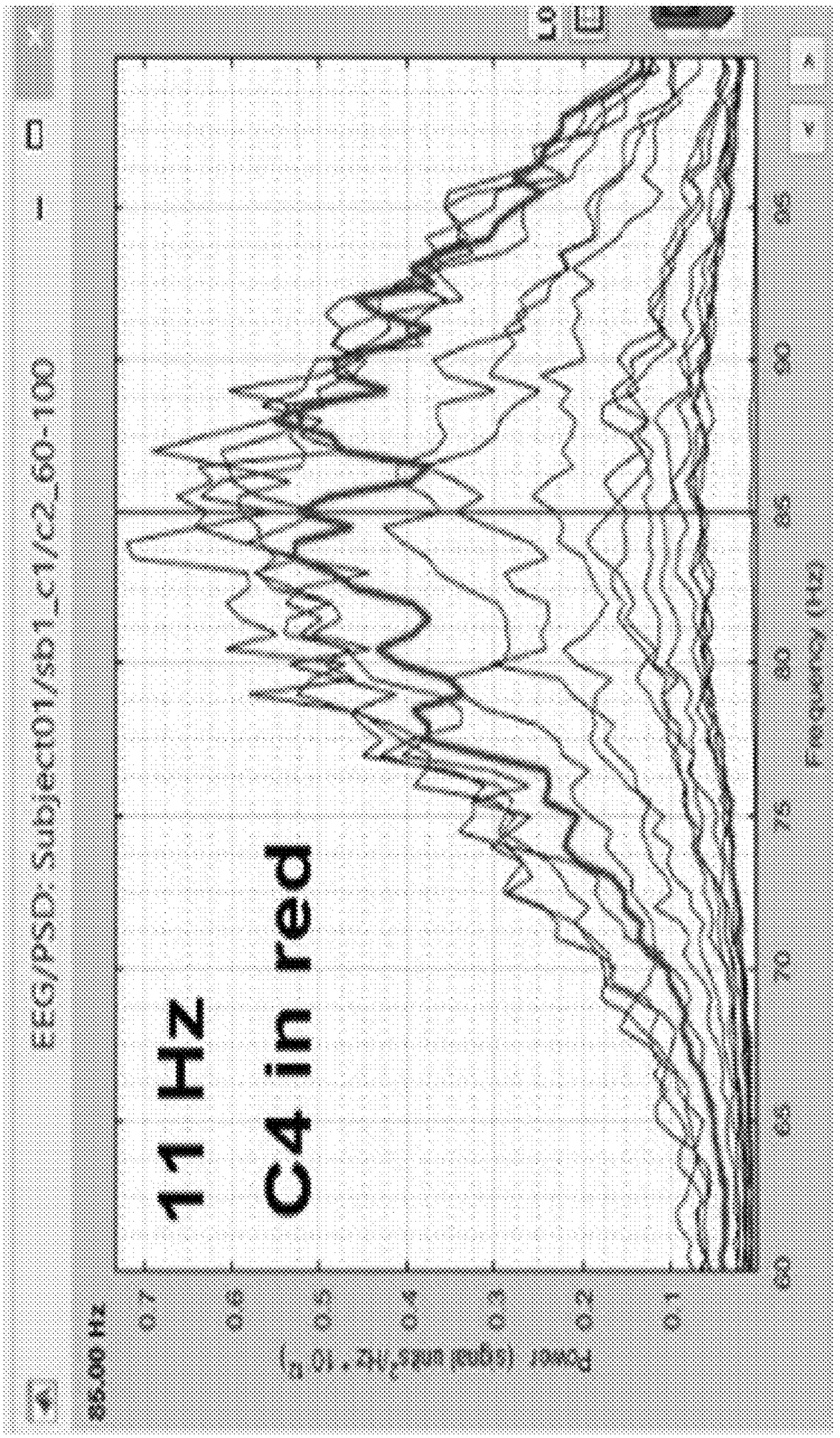
FIG. 24D is a series of spectral power plots from individual electrodes summarizing higher-frequency electrophysiological responses to tactile peripheral stimulation patterns administered at a frequency of 11 Hz.

FIG. 22A and FIG. 22C are topological maps summarizing changes in spectral power at lower frequencies in response to tactile stimulation administered at frequencies of 5 Hz and 11 Hz, respectively. FIGS. 22B and 22D are power spectra summarizing changes in spectral power at individual EEG electrodes at lower frequencies in response to tactile stimulations administered at frequencies of 5 Hz and 11 Hz, respectively. FIG. 24A and FIG. 24C are topological maps summarizing changes in spectral power at higher frequencies in response to tactile stimulation administered at frequencies of 5 Hz and 11 Hz, respectively. FIGS. 24B and 24D are power spectra summarizing changes in spectral power at individual EEG electrodes at higher frequencies in response to tactile stimulation administered at frequencies of 5 Hz and 11 Hz, respectively. FIG. 23A and FIG. 23C are topological maps summarizing changes in spectral power at higher frequencies in response to tactile stimulation administered at frequencies of 5 Hz and 11 Hz, respectively. FIGS. 23B and 23D are power spectra summarizing changes in spectral power at individual EEG electrodes at higher frequencies in response to tactile stimulation administered at frequencies of 5 Hz and 11 Hz, respectively. Tactile stimulation at 5 Hz induced higher changes in spectral power at lower frequencies relative to the changes included by tactile stimulation at 11 Hz. Tactile stimulation at 5 Hz and 11 Hz induced comparable changes in spectral power at higher frequencies.

What is claimed is:

1. A brain-computer interface (BCI) system, comprising:
- a neural activity sensor configured to monitor a series of neural activity signals indicative of a neural state of a subject;
- a peripheral stimulation device configured to administer a series of peripheral stimulations to the subject; and
- a computing device operatively coupled to the neural activity sensor and to the peripheral stimulation device, the computing device comprising at least one processor, wherein the at least one processor is configured to:
- receive the series of neural activity signals from the neural activity sensor; and
- iteratively generate and administer the series of peripheral stimulations to modify the neural state of the subject from a baseline state to a target state without volitional input from the subject, wherein iteratively generating and administering the series of peripheral stimulations comprises:
  - determining the baseline state based on a first set of neural activity signals of the series of neural activity signals,
  - applying a first series of peripheral stimulations to the subject using the peripheral stimulation device, the first series including a first plurality of peripheral stimulations each peripheral stimulation of the plurality of peripheral stimulations different than each other peripheral stimulation,
  - determining one or more first neural states based on a second set of neural activity signals received during and after applying the first series of peripheral stimulations received first signals,
  - determining, using an artificial intelligence model, a second series of peripheral stimulations different than the first series based on the first series of peripheral stimulations and changes between the baseline state and the one or more first neural states brought about by the first series of peripheral stimulations without volitional input from the subject, and
- applying the second series of peripheral stimulations to the subject using the peripheral stimulation device.

2. The system of claim 1, wherein the neural activity sensor is selected from at least one electroencephalographic (EEG) electrode, at least one single neuron recording electrode, at least one electrocorticography (ECOG) electrode, a functional magnetic resonance imaging (fMRI) scanner, a magnetoencephalographic (MEG) magnetometer, and at least one functional optical coherence tomography (fOCT) sensor.

3. The system of claim 2, wherein the peripheral stimulation device is selected from a pressure stimulation device, a vibrational stimulation device, an auditory stimulation device, a visual stimulation device, and any combination thereof.

4. The system of claim 3, wherein the at least one processor is further configured to receive the target state from an operator of the system.

5. The system of claim 1, wherein the artificial intelligence model is configured to reconfigure the series of peripheral stimulations based on changes in the series of neural activity signals.

6. The system of claim 5, wherein the artificial intelligence model is a genetic algorithm.

7. A computer-implemented method for modifying a neural state of a subject in need, the method comprising:
- providing a brain-computer interface (BCI) system comprising:
- a neural activity sensor configured to detect a plurality of neural activity signals indicative of a neural state of the subject;
- a peripheral stimulation device configured to administer a plurality of peripheral stimulations to the subject; and
- a computing device operatively coupled to the neural activity sensor and to the peripheral stimulation device, the computing device comprising at least one processor;
- receiving, using the computing device, a target neural state from an operator of the system;
- detecting, at the neural activity sensor, a plurality of baseline neural activity signals indicative of a baseline neural state of the subject;
- transforming, using the computing device, the plurality of baseline neural activity signals into a first series of peripheral stimulation patterns according to an artificial intelligence model;
- administering, using the peripheral stimulation device, a first peripheral stimulation to the subject, the first peripheral stimulation defined by the first series of peripheral stimulation patterns;
- detecting, at the neural activity sensor, a plurality of modified neural activity signals indicative of a modified neural state of the subject;
- determining, using the artificial intelligence model, a second series of peripheral stimulation patterns different than the first series of peripheral stimulation patterns based on the first series of peripheral stimulation patterns and changes between the baseline neural state of the subject and the one or modified neural state of the subject brought about by the first peripheral stimulation of the subject without volitional input from the subject; and
- administering, using the peripheral stimulation device, a second peripheral stimulation to the subject, the second peripheral stimulation defined by the second series of peripheral stimulation patterns.

8. The method of claim 7, wherein the neural activity sensor is selected from at least one electroencephalographic (EEG) electrode, at least one single neuron recording electrode, at least one electrocorticography (ECOG) electrode, a functional magnetic resonance imaging (fMRI) scanner, a magnetoencephalographic (MEG) magnetometer, and at least one functional optical coherence tomography (fOCT) sensor.

9. The method of claim 8, wherein the peripheral stimulation device is selected from a pressure stimulation device, a vibrational stimulation device, an auditory stimulation device, a visual stimulation device, and any combination thereof.

10. The method of claim 9, wherein transforming, using the computing device, the plurality of baseline neural activity signals into a peripheral stimulation pattern according to the artificial intelligence model further comprises reconfiguring, using the artificial intelligence model, the plurality of baseline peripheral stimulations based on changes in the plurality of neural activity signals.

11. The method of claim 10, wherein the artificial intelligence model is a genetic algorithm.

12. At least one non-transitory computer-readable storage media having computer-executable instructions embodied thereon, wherein when executed by at least one processor, the computer-executable instructions cause the at least one processor to:

receive a target neural state from an operator of the system;

receive a plurality of baseline neural activity signals indicative of a baseline neural state of the subject from a neural activity sensor;

transform the plurality of baseline neural activity signals into a first series of peripheral stimulation patterns according to an artificial intelligence model;

operate a peripheral stimulation device to administer a first peripheral stimulation to the subject, the first peripheral stimulation defined by the first series of peripheral stimulation patterns;

receive a plurality of modified neural activity signals indicative of a modified neural state of the subject from the neural activity sensor;

determine, using the artificial intelligence model, a second series of peripheral stimulation patterns different than the first series of peripheral stimulation patterns based on the first series of peripheral stimulation patterns and changes between the baseline neural state of the subject and the one or modified neural state of the subject brought about by the first peripheral stimulation of the subject without volitional input from the subject; and operate the peripheral stimulation device to administer a second peripheral stimulation to the subject, the second peripheral stimulation defined by the second series of peripheral stimulation patterns.

13. The at least one non-transitory computer-readable storage media of claim 12, wherein the neural activity sensor is selected from at least one electroencephalographic (EEG) electrode, at least one single neuron recording electrode, at least one electrocorticography (ECOG) electrode, a functional magnetic resonance imaging (fMRI) scanner, a magnetoencephalographic (MEG) magnetometer, and at least one functional optical coherence tomography (fOCT) sensor.

14. The at least one non-transitory computer-readable storage media of claim 13, wherein the peripheral stimulation device is selected from a pressure stimulation device, a vibrational stimulation device, an auditory stimulation device, a visual stimulation device, and any combination thereof.

15. The at least one non-transitory computer-readable storage media of claim 14, wherein the artificial intelligence model is a genetic algorithm.

16. The system of claim 1, wherein determining the second series of peripheral stimulations comprises determining, using the artificial intelligence model, the second series of peripheral stimulations to one of increase a prescribed neural activity signal of the subject or decrease a prescribed neural activity signal of the subject.

17. The system of claim 16 wherein the prescribed neural activity signal comprises one of a power in a specified frequency of the neural activity signals of the subject, a phase in a specified frequency of the neural activity signals of the subject, or a power in a specified location of a neural activity signal of the subject.

18. The system of claim 17, wherein the second series of peripheral stimulations is determined to increase the prescribed neural activity signal of the subject, the prescribed neural activity signal comprises the power in the specified frequency of the neural activity signals of the subject, and the specified frequency is one of a theta rhythm frequency, alpha rhythm frequency, beta rhythm frequency, delta rhythm frequency or a gamma rhythm frequency.

19. The system of claim 17, wherein the second series of peripheral stimulations is determined to decrease the prescribed neural activity signal of the subject, the prescribed neural activity signal comprises the power in the specified frequency of the neural activity signals of the subject, and the specified frequency is a gamma rhythm frequency.

20. The method of claim 7, wherein determining the second series of peripheral stimulations comprises determining, using the artificial intelligence model, the second series of peripheral stimulations to one of increase a prescribed neural activity signal of the subject or decrease a prescribed neural activity signal of the subject.

21. The method of claim 20 wherein the prescribed neural activity signal comprises one of a power in a specified frequency of the neural activity signals of the subject, a phase in a specified frequency of the neural activity signals of the subject, or a power in a specified location of a neural activity signal of the subject.

22. The method of claim 21, wherein the second series of peripheral stimulations is determined to increase the prescribed neural activity signal of the subject, the prescribed neural activity signal comprises the power in the specified frequency of the neural activity signals of the subject, and the specified frequency is one of a theta rhythm frequency, alpha rhythm frequency, beta rhythm frequency, delta rhythm frequency or a gamma rhythm frequency.

23. The method of claim 21, wherein the second series of peripheral stimulations is determined to decrease the prescribed neural activity signal of the subject, the prescribed neural activity signal comprises the power in the specified frequency of the neural activity signals of the subject, and the specified frequency is a gamma rhythm frequency.

24. The at least one non-transitory computer-readable storage media of claim 12, wherein the instructions cause the at least one processor to determine the second series of peripheral stimulations by determining, using the artificial intelligence model, the second series of peripheral stimulations to one of increase a prescribed neural activity signal of the subject or decrease a prescribed neural activity signal of the subject.

25. The at least one non-transitory computer-readable storage media of claim 24 wherein the prescribed neural activity signal comprises one of a power in a specified frequency of the neural activity signals of the subject, a phase in a specified frequency of the neural activity signals of the subject, or a power in a specified location of a neural activity signal of the subject.

26. The at least one non-transitory computer-readable storage media of claim 25, wherein the second series of peripheral stimulations is determined to increase the prescribed neural activity signal of the subject, the prescribed neural activity signal comprises the power in the specified frequency of the neural activity signals of the subject, and the specified frequency is one of a theta rhythm frequency, alpha rhythm frequency, beta rhythm frequency, delta rhythm frequency or a gamma rhythm frequency.

27. The at least one non-transitory computer-readable storage media of claim 25, wherein the second series of peripheral stimulations is determined to decrease the prescribed neural activity signal of the subject, the prescribed neural activity signal comprises the power in the specified frequency of the neural activity signals of the subject, and the specified frequency is a gamma rhythm frequency.

* * * * *